US005290914A

United States Patent [19]

Wilcox et al.

[11] Patent Number: 5,290,914

[45] Date of Patent: Mar. 1, 1994

[54] HYBRID DIPHTHERIA-B.T. PESTICIDAL TOXINS

[75] Inventors: Edward Wilcox, Escondido; David L. Edwards, Del Mar; George E. Schwab, La Jolla; Mark Thompson, Del Mar; Paul Culver, Encinitas, all of Calif.

[73] Assignee: Mycogen Corporation, San Diego, Calif.

[21] Appl. No.: 187,167

[22] Filed: Apr. 28, 1988

[51] Int. Cl.[5] ...................... C07K 13/00; C12P 21/06; C12N 15/00

[52] U.S. Cl. .................................. 530/350; 424/93 L; 935/47; 435/69.7

[58] Field of Search ................. 435/69.7, 194; 935/47; 530/350

[56] References Cited

U.S. PATENT DOCUMENTS

| | | | |
|---|---|---|---|
| 4,467,036 | 8/1984 | Schnepf et al. . | |
| 4,695,455 | 9/1987 | Barnes et al. | 424/93 |
| 4,830,692 | 5/1989 | Gelfand et al. | 435/68 |
| 4,870,023 | 9/1989 | Fraser et al. | 435/320 |

OTHER PUBLICATIONS

Knowles, B. H., W. E. Thomas and D. J. Ellar (1984) "Lectin-Like Binding or *Bacillus thuringiensis* var kurstaki Lepidopteran-Specific Toxin is an Initial Step in Insecticidal Action," FEBS 168(2):197-202.

Schnepf, H. E., and H. R. Whiteley (1985) "Delineation of a Toxin-Encoding Segment of a *Bacillus thuringiensis* Crystal Protein Gene," J. Biol. Chem. 260:6273-6290.

Pennock et al. "Strong and Regulated Expression of *Escherichia coli* βGalactosidase in Insect cells . . . " *Molec. and Cell. Biology* vol. 4, #3 pp. 399-406 1984.

Stirpe, et al "Ribosome-Inactivating Proteins up to date" FEBS 3269 vol. 195, Nos. 1,2, pp. 1-8 1986.

*Primary Examiner*—Robert A. Wax
*Assistant Examiner*—Keith D. Hendricks
*Attorney, Agent, or Firm*—Saliwanchik & Saliwanchik

[57] ABSTRACT

The invention concerns novel hybrid pesticidal toxins. These toxins are expressed as the fusion protein of a chimeric gene. Specifically exemplified is a novel *B.t.* hybrid toxin. These novel toxins have increased toxicity against target pests. The invention also concerns a process for preparing a hybrid virus having an altered insect host range.

2 Claims, 19 Drawing Sheets

```
                     1      620       1239       1859      2479      3098       3718
Enzyme      No. Cuts +---------|----------|---------|---------|----------|---------->
Acc1               2.                   1           1
AflIII             3.         1                                    1       1
AluI              10.       1         1    1    2               1   2        11
Asp718             1.                                    1
AsuII              1.            1
AvaI               1.                              1
AvrII              2.                    1                     1
BanI               1.                                    1
BanII              1.                       1
BbvI has no cut site
BclI               2.                               1             1
BglI               1.                    1
BinI has no cut site
BsmI               5.2                             1               1 1
BspMI has no cut site
BspMII             1.                                                        1
BssHII             1.                                         1
CfrI has no cut site
Cfr1OI has no cut site
ClaI               4. 1                   1               1  1
DdeI               8.    1        1          1        1    1 11     1
DpnI               6.     1                         1          1  1      1     1
DraI               3.                                    1                      1  1
DraII              1.                                          1
EcoRI              2.   1            1
EcoRI'            32. 12121 11 1 2   1 211111     3  12    1 1  1 1           1  1
EcoRI*            45.12131111  223   1  2  2 112  2 122 121      1 11       1  111
EcoRV              3.            2             1
Fnu4HI             6.        11        1                     1      11
FnuDI              2.                1                      1
```

FIGURE 1A

```
                    1      620      1239      1859      2479      3098      3718
Enzyme     No. Cuts +--------|---------|---------|---------|---------|--------->
FnuDII            2.        1                             1
FokI has no cut site
GdiII             1.                                     1
GsuI has no cut site
HaeII             1.                                        1
HaeIII            2.               1                     1
HgaI              2.   1                                   1
HgiEII has no cut site
HhaI              5.                             2        2 1
HinDIII           1.                                            1
HinFI            16.    1     1  1     1     1      2  1  2 1 111     1  1
HinPI             5.                             2        2 1
HpaII             5.  1       1                                 1  11
HphI              4.                         1   1         1      1
KpnI              1.                                  1
MaeI             12.  111    11     1  1          1        13
MaeII            15.         1      1  1     11  1 1 12      1 1  1   11
MaeIII           12.11                       1  1 11  1              1111   1
MboI              6.     1                        1        1  1      1     1
MboII            15.   1 1    11     1         1        1   1    1 1  1211
MnlI has no cut site
NheI              1.                                        1
NlaIII            8.      1             1           1   1      2  1  1
NlaIV             8.  1 1     1    1  1               1  1              1
NsiI              2.1                                                   1
NspBII            3.                  1                                 11
NspCI             2.                                1             1
PstI              2.                      1     1
PvuII             2.                                                    11
RsaI             14.   1     2               11     11   1 1        1  21  1
```

FIGURE 1B

INHIBITION OF CF-1 CELL PROTEIN SYNTHESIS BY HYBRID TOXINS

```
        10         20         30         40         50         60         70         80
GTGAGCAGAAAACTGTTTGCGTCAATCTTAATAGGGGCGCTACTGGGATAGGGGCCCCACCTTCAGCCCATGCAGGCGC

        90        100        110        120        130        140        150        160
TGATGATGTTGTTGATTCTTCTAAATCTTTTGTGATGGAAAACTTTTCTTCGTACCACGGACTAAACCTGGTTATGTAG

       170        180        190        200        210        220        230        240
ATTCCATTCAAAAAGGTATACAAAAGCCAAAATCTGGTACACAAGGAAATTATGACGATGATTGGAAAGGGTTTTATAGT

       250        260        270        280        290        300        310        320
ACCGACAATAAATACGACGCTGCGGGATACTCTGTAGATAATGAAAACCCGCTCTCTGGAAAAGCTGGAGGCGTGGTGAA

       330        340        350        360        370        380        390        400
AGTGACGTATCCAGGACTGACGAAGGTTCTCGCACTAAAAGTGGATAATGCCGAAACTATTAAGAAAGAGTTAGGTTTAA

       410        420        430        440        450        460        470        480
GTCTCACTGAACCGTTGATGGAGCAAGTCGGAACGGAAGAGTTTATCAAAAGGTTCGGTGATGGTGCTTCGCGTGTAGTG

       490        500        510        520        530        540        550        560
CTCAGCCTTCCCTTCGCTGAGGGGAGTTCTAGCGTTGAATATATTAATAACTGGGAACAGGCGAAAGCGTTAAGCGTAGA

       570        580        590        600        610        620        630        640
ACTTGAGATTAATTTTGAAACCCGTGGAAAACGTGGCCAAGATGCGATGTATGAGTATATGGCTCAAGCCTGTGCAGGAA

       650        660        670        680        690        700        710        720
ATCGTGTCAGGCGATCAGTAGGTAGCTCATTGTCATGCATAAATCTTGATTGGGATGTCATAAGGGATAAAACTAAGACA

       730        740        750        760        770        780        790        800
AAGATAGAGTCTTTGAAAGAGCATGGCCCTATCAAAAATAAAATGAGCGAAAGTCCCAATAAAACAGTATCTGAGGAAAA
```

FIGURE 8A

810 820 830 840 850 860 870 880
AGCTAAACAATACCTAGAAGAATTTCATCAAACGGCATTAGAGCATCCTGAATTGTCAGAACTTAAAACCGTTACTGGGA 890 900 910 920 930 940 950 960
CCAATCCTGTATTCGCTGGGGCTAACTATGCGGCGTGGCAGTAAACGTTGCGCAAGTTATCGATAGCGAAACAGCTGAT 970 980 990 1000 1010 1020 1030 1040
AATTTGGAAAAGACAACTGCTGCTCTTTCGATACTTCCTGGTATCGGTAGCGTAATGGGCATTGCAGACGGTGCCGTTCA 1050 1060 1070 1080 1090 1100 1110 1120
CCACAATACAGAAGAGATAGTGGCACAATCAATAGCTTTATCGTCTTTAATGGTTGCTCAAGCTATTCCATTGGTAGGAG 1130 1140 1150 1160 1170 1180 1190 1200
AGCTAGTTGATATTGGTTTCGCTGCATATAATTTTGTAGAGAGTATTATCAATTTATTTCAAGTAGTTCATAATTCGTAT 1210 1220 1230 1240 1250 1260 1270 1280
AATCGTCCCGCGTATTCTCCGGGGCATAAAACGCAACCATTTCTTCATGACGGGTATGCTGTCAGTTGGAACACTGTTGA 1290 1300 1310 1320 1330 1340 1350 1360
AGATTCGATAATCCGAACTGGTTTTCAAGGGGAGAGTGGCACGACATAAAAATTACTGCTGAAAATACCCCGCTTCCAA 1370 1380 1390 1400 1410 1420 1430 1440
TCGCGGGTGTCCTACTACCGACTATTCCTGGAAAGCTGGACGTTAATAAGTCCAAGACTCATATTTCCGTAAATGGTCGG 1450 1460 1470 1480 1490 1500 1510 1520
AAAATAAGGATGCGTTGCAGAGCTATAGACGGTGATGTAACTTTTTGTCGCCCTAAATCTCCTGTTTATGTTGGTAATGG

FIGURE 8B

```
      1530      1540      1550      1560      1570      1580      1590      1600
TGTGCATGCTAACCTGTTTCGAACAGTTTCCCAATTAACAAGAGAAATTTATACAAACCCAGTATTAGAAAATTTTGATG

      1610      1620      1630      1640      1650      1660      1670      1680
GTAGTTTTCGAGGCTCGGCTCAGGGCATAGAAAGAAGTATTAGGAGTCCACATTTGATGGATATACTTAACAGTATAACC

      1690      1700      1710      1720      1730      1740      1750      1760
ATCTATACGGATGCTCATAGGGGTTATTATTATTGGTCAGGGCATCAAATAATGGCTTCTCCTGTAGGGTTTTCGGGGCC

      1770      1780      1790      1800      1810      1820      1830      1840
AGAATTCACTTTTCCGCTATATGCAACTATGGGAAATGCAGCTCCACAACAACGTATTGTTGCTCAACTAGGTCAGGGCG

      1850      1860      1870      1880      1890      1900      1910      1920
TGTATAGAACATTATCGTCCACTTTATATAGAAGACCTTTTAATATAGGGATAAATAATCAACAACTATCTGTTCTTGAC

      1930      1940      1950      1960      1970      1980      1990      2000
GGGACAGAATTTGCTTATGGAACCTCCTCAAATTTGCCATCCGCTGTATACAGAAAAAGCGGAACGGTAGATTCGCTGGA

      2010      2020      2030      2040      2050      2060      2070      2080
TGAAATACCGCCACAGAATAACAACGTGCCACCTAGGCAAGGATTTAGTCATCGATTAAGCCATGTTTCAATGTTTCGTT
```

FIGURE 8C

```
      2090      2100      2110      2120      2130      2140      2150      2160
CAGGCTTTAGTAATAGTAGTGTAAGTATAATAAGAGCTCCTATGTTCTCTTGGATACATCGTAGTGCTGAATTTAATAAT

      2170      2180      2190      2200      2210      2220      2230      2240
ATAATTGCATCGGATAGTATTACTCAAATCCCTGCAGTGAAGGGAAACTTTCTTTTTAATGGTTCTGTAATTTCAGGACC

      2250      2260      2270      2280      2290      2300      2310      2320
AGGATTTACTGGTGGGGACTTAGTTAGATTAAATAGTAGTCGAAATAACATTCAGAATAGAGGGTATATTGAAGTTCCAA

      2330      2340      2350      2360      2370      2380      2390      2400
TTCACTTCCCATCGACATCTACCAGATATCGAGTTCGTGTACGGTATGCTTCTGTAACCCCGATTCACCTCAACGTTAAT

      2410      2420      2430      2440      2450      2460      2470      2480
TGGGGTAATTCATCCATTTTTTCCAATACAGTACCAGCTACAGCTACGTCATTAGATAATCTACAATCAAGTGATTTTGG

      2490      2500      2510      2520      2530      2540      2550      2560
TTATTTTGAAAGTCGCAATGCTTTTACATCTTCATTAGGTAATATAGTAGGTGTTAGAAATTTTAGTGGACTGCAGGAG

      2570      2580      2590      2600      2610      2620
TGATAATAGACAGATTTGAATTTATTCCAGTTACTGCAACACTCGAGTAGTAGGTCGACAGCTT
```

FIGURE 8D

```
     10        20        30        40        50        60        70        80
GTGAGCAGAAAACTGTTTGCGTCAATCTTAATAGGGGCGCTACTGGGGATAGGGGCCCCACCTTCAGCCCATGCAGGCGC

     90       100       110       120       130       140       150       160
TGATGATGTTGTTGATTCTTCTAAATCTTTTGTGATGGAAAACTTTTCTTCGTACCACGGGACTAAACCTGGTTATGTAG

    170       180       190       200       210       220       230       240
ATTCCATTCAAAAAGGTATACAAAAGCCAAAATCTGGTACACAAGGAAATTATGACGATGATTGGAAAGGGTTTTATAGT

    250       260       270       280       290       300       310       320
ACCGACAATAAATACGACGCTGCGGGATACTCTGTAGATAATGAAAACCCGCTCTCTGGAAAAGCTGGAGGCGTGGTGAA

    330       340       350       360       370       380       390       400
AGTGACGTATCCAGGACTGACGAAGGTTCTCGCACTAAAAGTGGATAATGCCGAAACTATTAAGAAAGAGTTAGGTTTAA

    410       420       430       440       450       460       470       480
GTCTCACTGAACCGTTGATGGAGCAAGTCGGAACGGAAGAGTTTATCAAAAGGTTCGGTGATGGTGCTTCGCGTGTAGTG

    490       500       510       520       530       540       550       560
CTCAGCCTTCCCTTCGCTGAGGGGAGTTCTAGCGTTGAATATATTAATAACTGGGAACAGGCGAAAGCGTTAAGCGTAGA

    570       580       590       600       610       620       630       640
ACTTGAGATTAATTTTGAAACCCGTGGAAAACGTGGCCAAGATGCGATGTATGAGTATATGGCTCAAGCCTGTGCAGGAA

    650       660       670       680       690       700       710       720
ATCGTGTCAGGCGATCAGTAGGTAGCTCATTGTCATGCATAAATCTTGATTGGGATGTCATAAGGGATAAAACTAAGACA

    730       740       750       760       770       780       790       800
AAGATAGAGTCTTTGAAAGAGCATGGCCCTATCAAAAATAAAATGAGCGAAAGTCCCAATAAAACAGTATCTGAGGAAAA
```

FIGURE 9A

```
        810        820        830        840        850        860        870        880
AGCTAAACAATACCTAGAAGAATTTCATCAAACGGCATTAGAGCATCCTGAATTGTCAGAACTTAAAACCGTTACTGGGA

        890        900        910        920        930        940        950        960
CCAATCCTGTATTCGCTGGGGCTAACTATGCGGCGTGGCAGTAAACGTTGCGCAAGTTATCGATAGCGAAACAGCTGAT

        970        980        990       1000       1010       1020       1030       1040
AATTTGGAAAAGACAACTGCTGCTCTTTCGATACTTCCTGGTATCGGTAGCGTAATGGGCATTGCAGACGGTGCCGTTCA

       1050       1060       1070       1080       1090       1100       1110       1120
CCACAATACAGAAGAGATAGTGGCACAATCAATAGCTTTATCGTCTTTAATGGTTGCTCAAGCTATTCCATTGGTAGGAG

       1130       1140       1150       1160       1170       1180       1190       1200
AGCTAGTTGATATTGGTTTCGCTGCATATAATTTTGTAGAGAGTATTATCAATTTATTTCAAGTAGTTCATAATTCGTAT

       1210       1220       1230       1240       1250       1260       1270       1280
AATCGTCCCGCGTATTCTCCGGGGCATAAAACGCAACCATTTCTTCATGACGGGTATGCTGTCAGTTGGAACACTGTTGA

       1290       1300       1310       1320       1330       1340       1350       1360
AGATTCGATAATCCGAACTGGTTTTCAAGGGGAGAGTGGGCACGACATAAAAATTACTGCTGAAAATACCCCGCTTCCAA

       1370       1380       1390       1400       1410       1420       1430       1440
TCGCGGGTGTCCTACTACCGACTATTCCTGGAAAGCTGGACGTTAATAAGTCCAAGACTCATATTTCCGTAAATGGTCGG

       1450       1460       1470       1480       1490       1500       1510       1520
AAAATAAGGATGCGTTGCAGAGCTATAGACGGTGATGTAACTTTTTGTCGCCCTAAATCTCCTGTTTATGTTGGTAATGG
```

FIGURE 9B

```
      1530       1540       1550       1560       1570       1580       1590       1600
TGTGCATGCAGGTGCAGCTCCTATGTTCTCTTGGATACATCGTAGTGCTGAATTTAATAATATAATTGCATCGGATAGTA

      1610       1620       1630       1640       1650       1660       1670       1680
TTACTCAAATCCCTGCAGTGAAGGGAAACTTTCTTTTTAATGGTTCTGTAATTTCAGGACCAGGATTTACTGGTGGGGAC

      1690       1700       1710       1720       1730       1740       1750       1760
TTAGTTAGATTAAATAGTAGTCGAAATAACATTCAGAATAGAGGGTATATTGAAGTTCCAATTCACTTCCCATCGACATC

      1770       1780       1790       1800       1810       1820       1830       1840
TACCAGATATCGAGTTCGTGTACGGTATGCTTCTGTAACCCCGATTCACCTCAACGTTAATTGGGGTAATTCATCCATTT

      1850       1860       1870       1880       1890       1900       1910       1920
TTTCCAATACAGTACCAGCTACAGCTACGTCATTAGATAATCTACAATCAAGTGATTTTGGTTATTTTGAAAGTCGCAAT

      1930       1940       1950       1960       1970       1980       1990       2000
GCTTTTACATCTTCATTAGGTAATATAGTAGGTGTTAGAAATTTTAGTGGACTGCAGGAGTGATAATAGACAGATTTGA

      2010       2020       2030       2040
ATTTATTCCAGTTACTGCAACACTCGAGTAGTAGGTCGACAGCTT
```

```
  1  M S R K L F A S I L I G A L L G I G A P P S A H A G A D D V
 31  V D S S K S F V M E N F S S Y H G T K P G Y V D S I Q K G I
 61  Q K P K S G T Q G N Y D D D W K G F Y S T D N K Y D A A G Y
 91  S V D N E N P L S G K A G G V V K V T Y P G L T K V L A L K
121  V D N A E T I K K E L G L S L T E P L M E Q V G T E E F I K
151  R F G D G A S R V V L S L P F A E G S S S V E Y I N N W E Q
181  A K A L S V E L E I N F E T R G K R G Q D A M Y E Y M A Q A
211  C A G N R V R R S V G S S L S C I N L D W D V I R D K T K T
241  K I E S L K E H G P I K N K M S E S P N K T V S E E K A K Q
271  Y L E E F H Q T A L E H P E L S E L K T V T G T N P V F A G
301  A N Y A A W A V N V A Q V I D S E T A D N L E K T T A A L S
331  I L P G I G S V M G I A D G A V H H N T E E I V A Q S I A L
361  S S L M V A Q A I P L V G E L V D I G F A A Y N F V E S I I
391  N L F Q V V H N S Y N R P A Y S P G H K T Q P F L H D G Y A
421  V S W N T V E D S I I R T G F Q G E S G H D I K I T A E N T
451  P L P I A G V L L P T I P G K L D V N K S K T H I S V N G R
481  K I R M R C R A I D G D V T F C R P K S P V Y V G N G V H A
511  N L F R T V S Q L T R E I Y T N P V L E N F D G S F R G S A
541  Q G I E R S I R S P H L M D I L N S I T I Y T D A H R G Y Y
571  Y W S G H Q I M A S P V G F S G P E F T F P L Y G T M G N A
601  A P Q Q R I V A Q L G Q G V Y R T L S S T L Y R R P F N I G
```

| | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|
|631|I|N|N|Q|L|L|S|V|D|G|T|E|F|A|Y|G|V|P|T|S|S|Q|S|N|L|P|S|A|V|Y|R|K|S|
|661|G|T|V|D|S|L|D|I|P|P|Q|N|N|V|P|P|M|F|L|F|N|G|W|F|S|H|R|L|S|H|V|S|N|
|691|M|F|R|S|G|F|S|P|S|A|N|H|I|R|A|N|F|L|N|R|G|Y|I|E|V|P|S|A|E|F|N|T|T|
|721|H|I|A|D|S|N|T|A|V|N|V|R|A|P|N|F|N|R|G|V|N|W|G|P|I|H|F|P|I|G|P|G|S|
|751|G|T|R|L|I|R|T|V|N|N|V|K|G|Q|F|P|M|L|F|N|Y|P|A|H|S|S|I|H|F|P|S|N|T|
|781|T|Y|R|V|V|L|V|T|P|A|N|N|I|Q|N|F|N|L|N|V|F|D|T|N|S|A|N|F|S|S|S|L|T|
|811|V|R|R|R|R|R|R|D|Q|S|A|V|K|H|H|R|G|N|F|E|Y|F|H|A|N|F|P|T|S|L|L|G|I|
|841|P|A|A|T|T|N|L|S|A|G|S|N|T|I|P|L|R|G|E|F|A|G|F|S|F|V|T|N|L|E|L|
|871|N|V|V|V|V|V|G|R|N|T|A|G|V|I|D|F|F|I|P|V|T|A|T|T|L|E|G|L|

```
  1  M S R K L F A S I L I G A L L G I G A P P S A H A G A D D V
 31  V D S S K S F V M E N F S S Y H G T K P G Y V D S I Q K G I
 61  Q K P K S G T Q G N Y D D D W K G F Y S T D N K Y D A A G Y
 91  S V D N E N P L S G K A G G V V K V T Y P G L T K V L A L K
121  V D N A E T I K K E L G L S L T E P L M E Q V G T E E F I K
151  R F G D G A S R V V L S L P F A E G S S S V E Y I N N W E Q
181  A K A L S V E L E I N F E T R G K R G Q D A M Y E Y M A Q A
211  C A G N R V R R S V G S S L S C I N L D W D V I R D K T K T
241  K I E S L K E H G P I K N K M S E S P N K T V S E E K A K Q
271  Y L E E F H Q T A L E H P E L S E L K T V T G T N P V F A G
301  A N Y A A W A V N V A Q V I D S E T A D N L E K T T A A L S
331  I L P G I G S V M G I A D G A V H H N T E E I V A Q S I A L
361  S S L M V A Q A I P L V G E L V D I G F A A Y N F V E S I I
391  N L F Q V V H N S Y N R P A Y S P G H K T Q P F L H D G Y A
421  V S W N T V E D S I I R T G F Q G E S G H D I K I T A E N T
451  P L P I A G V L L P T I P G K L D V N K S K T H I S V N G R
481  K I R M R C R A I D G D V T F C R P K S P V Y V G N G V H A
511  G A A P M F S W I H R S A E F N N I I A S D S I T Q I P A V
541  K G N F L F N G S V I S G P G F T G G D L V R L N S S G N N
571  I Q N R G Y I E V P I H F P S T S T R Y R V R V R Y A S V T
601  P I H L N V N W G N S S I F S N T V P A T A T S L D N L Q S
631  S D F G Y F E S A N A F T S S L G N I V G V R N F S G T A G
661  V I I D R F E F I P V T A L E
691
```

HYBRID DIPHTHERIA-B.T. PESTICIDAL TOXINS

BACKGROUND OF THE INVENTION

*Bacillus thuringiensis* (*B.t.*) is widely used for the microbial control of insects. The active component has been identified as a proteinaceous paraspore also described as a crystal. Following ingestion by the insect host the crystal is processed by gut proteases to the active protease-resistant form which is toxic. Toxicity is postulated to follow binding of the active form of the toxin to the insect cells resulting in disruption of cellular integrity through a receptor mediated process (Knowles, B.H. et al. [1984] FEBS 168:197-202).

A comparison of amino acid sequence for the protease activated form of *B. thuringiensis* var. kurstaki HD-1 and HD-73 reveals that the amino-terminal (N-terminal) half of the protein is highly conserved whereas the carboxy-terminal (C-terminal) is highly substituted in sequence. In U.S. Pat. No. 4,467,036 *B. thuringiensis* var. kurstaki HD-1 is disclosed as being available from the NRRL culture repository at Peoria, Ill. Its accession number is NRRL B-3792. *B. thuringiensis* var. kurstaki HD-73 is also available from the NRRL under accession number NRRL B-4488.

In addition to HD-1 and HD-73, the presence of an N-terminal conserved or constant region and a C-terminal highly substituted or variable region in the active toxin has been demonstrated for *B. thuringiensis* var. berliner and var. aizawa.

Schnepf, E. H. and Whitely, H. R. (1985) J. Biol. Chem. 260:6273-6290 have demonstrated that deletions of the amino and carboxy termini result in a loss of toxicity indicating that both regions of the active toxin are required for toxicity.

BRIEF SUMMARY OF THE INVENTION

The subject invention concerns novel hybrid pesticidal toxins. Specifically exemplified is an insecticidal fusion protein expressed as a single polypeptide product of a hybrid gene comprising a cytotoxic agent and a specific insect gut cell recognition ("binding") protein to direct the cytotoxic agent to the host target. Details for the construction of a hybrid B.t. toxin are disclosed. The cytotoxic agent is an ADP-ribosylating enzyme. For example, the cytotoxic agent can be the A fragment of the diphtheria toxin, plus the B fragment of the diphtheria toxin which has been truncated at the carboxyl-terminus to remove the eukaryotic binding region. The diphtheria toxin gene 3′ recognition domain is replaced with a synthetic DNA linker region to which a gene encoding the insect gut epithelial cell recognition portion of *Bacillus thuringiensis* var. kurstaki HD-73 is ligated.

The purpose of the synthetic DNA linker is to join pieces of otherwise non-ligating segments of DNA. In the subject invention, it is a critical element of the invention because it must be of a suitable length and amino acid composition to minimize susceptibility to insect protease cleavage. Thus, the peptide linker should be as short as possible, e.g., four or less amino acids, and it should not contain lysine residues. There are other considerations in the use of a suitable linker. For example, the linker should maintain the correct reading frame and it should maintain a continuum in the hydropathy profile of the primary structure of the protein.

The novel hybrid *B.t.* gene can be transformed into a suitable host to produce the toxin which can be recovered by standard biochemical procedures. Alternatively, the transformed host containing the novel hybrid *B.t.* gene can be used per se as an insecticide, as disclosed hereinafter. Though B.t.k. HD-73 is specifically exemplified herein, the invention includes other microbial insecticides.

Table 1 gives molecular weights of polypeptides present in SeNPV and HzNPV LOVAL preparations determined from relative electrophoretic mobilities.

Table 2 shows hybrid virus infectivity.

Table 3 gives relative molecular weights of polypeptides as determined by electrophoretic mobility.

The process, described herein, can be applied to the C-terminal variable portion of active *B. thuringiensis* toxins other than var. kurstaki HD-73. These include those *B.t,*'s possess a variable region in the C-terminal half of the active toxin. Examples of such *B.t.*'s are *B.t.* var. israelensis, active against mosquitoes; B.t. var. san diego and B.t. var. tenebrionis, active against coleoptera; and *B. sphaericus,* active against mosquito larvae. Cultures exemplifying the above are as follows:

*Bacillus thuringiensis* var. kurstaki HD-1--NRRL B-3792; disclosed in U.S. Pat. No. 4,448,885
*Bacillus thuringiensis* var. israelensis--ATCC 35646
*Bacillus thuringiensis* var. san diego--NRRL B-15939

The following *B. thuringiensis* cultures are available from the United States Department of Agriculture (USDA) at Brownsville, Tex. Requests should be made to Joe Garcia, USDA, ARS, Cotton Insects Research Unit, P.O. Box 1033, Brownsville, Tex. 78520 USA.

*B. thuringiensis* HD2
*B. thuringiensis* var. finitimus HD3
*B. thuringiensis* var. alesti HD4
*B. thuringiensis* var. kurstaki HD73
*B. thuringiensis* var. sotto HD770
*B. thuringiensis* var. dendrolimus HD7
*B. thuringiensis* var. kenyae HD5
*B. thuringiensis* var. galleriae HD29
*B. thuringiensis* var. canadensis HD2
*B. thuringiensis* var. entomocidus HD9
*B. thuringiensis* var. subtoxicus HD109
*B. thuringiensis* var. aizawai HD11
*B. thuringiensis* var. morrisoni HD12
*B. thuringiensis* var. ostriniae HD501
*B. thuringiensis* var. tolworthi HD537
*B. thuringiensis* var. darmstadiensis HD146
*B. thuringiensis* var. toumanoffi HD201
*B. thuringiensis* var. kyushuensis HD541
*B. thuringiensis* var. thompsoni HD542
*B. thuringiensis* var. pakistani HD395
*B. thuringiensis* var. israelensis HD567
*B. thuringiensis* var. indiana HD521
*B. thuringiensis* var. dakota
*B. thuringiensis* var. tohokuensis HD866
*B. thuringiensis* var. kumanotoensis HD867
*B. thuringiensis* var. tochigiensis HD868
*B. thuringiensis* var. colmeri HD847
*B. thuringiensis* var. wuhanensis HD525

Other pesticidal toxins which can be used include those of entomopathogenic fungi, such as beauverin of *Beauveria bassiana* and destruxins of Metarrhizium spp.; or the broad spectrum insecticidal compounds, such as the avermectins of *Streptomyces avermitilus.* Cultures exemplifying the above are as follows:

*Bacillus cereus*—ATCC 21281
*Bacillus moritai*—ATCC 21282

*Bacillus popilliae*—ATCC 14706
*Bacillus lentimorbus*—ATCC 14707
*Bacillus sphaericus*—ATCC 33203
*Beauveria bassiana*—ATCC 9835
*Metarrhizium anisopliae*—ATCC 24398
*Metarrhizium flavoviride*—ATCC 32969
*Streptomyces avermitilus*—ATCC 31267

The technology of the invention is not limited to the use of diphtheria toxin as the cytotoxic agent as a variety of enzymes that inhibit protein synthesis can be used, for example, the ribosome inactivators such as ricin, dianthin, saporin, gelonin, tritin, abrin, and modeccin, as well as enzymes from barley seeds, rye seeds, wild beans, and corn seeds (see Stripe, F., and Barbieri, L., [1986] FEBS 195:1-8).

The subject invention is not limited to toxins active against insects, but also includes *B. thuringiensis* toxins active against animal parasitic nematodes, and plant parasitic nematodes. In general, any pesticide can be used. For example, it can be a polypeptide which has toxic activity toward a eukaryotic multicellular pest, such as insects, e.g., coleoptera, lepidoptera, diptera, hemiptera, dermaptera, and orthoptera; or arachnids; gastropods; or worms, such as nematodes and platyhelminths. Various susceptible insects include beetles, moths, flies, grasshoppers, lice, and earwigs.

The subject invention also includes a process for altering the insect host range of a nuclear polyhedrosis virus (NPV) by re-associating solubilized envelope proteins from one occluded NPV to another to produce a hybrid virus having an altered NPV insect host range.

DNA encoding half-length hybrid toxin

FIG. 8

```
10 20 30 40 50 60 70 80
GTGAGCAGAAAACTGTTTGCGTCAATCTTAATAGGGGCGCTACTGGGGATAGGGGCCCCACCTTCAGCCCATGCAGGCGC
90 100 110 120 130 140 150 160
TGATGATGTTGTTGATTCTTCTAAATCTTTTGTGATGGAAAACTTTTCTTCGTACCACGGGACTAAACCTGGTTATGTAG
170 180 190 200 210 220 230 240
ATTCCATTCAAAAAGGTATACAAAAGCCAAAATCTGGTACACAAGGAAATTATGACGATGATTGGAAAGGGTTTTATAGT
250 260 270 280 290 300 310 320
ACCGACAATAAATACGACGCTGCGGGATACTCTGTAGATAATGAAAACCCGCTCTCTGGAAAAGCTGGAGGCGTGGTGAA
330 340 350 360 370 380 390 400
AGTGACGTATCCAGGACTGACGAAGGTTCTCGCACTAAAAGTGGATAATGCCGAAACTATTAAGAAAGAGTTAGGTTTAA
410 420 430 440 450 460 470 480
GTCTCACTGAACCGTTGATGGAGCAAGTCGGAACGGAAGAGTTTATCAAAAGGTTCGGTGATGGTGCTTCGCGTGTAGTG
490 500 510 520 530 540 550 560
CTCAGCCTTCCCTTCGCTGAGGGGAGTTCTAGCGTTGAATATATTAATAACTGGGAACAGGCGAAAGCGTTAAGCGTAGA
570 580 590 600 610 620 630 640
ACTTGAGATTAATTTTGAAACCCGTGGAAAACGTGGCCAAGATGCGATGTATGAGTATATGGCTCAAGCCTGTGCAGGAA
650 660 670 680 690 700 710 720
ATCGTGTCAGGCGATCAGTAGGTAGCTCATTGTCATGCATAAATCTTGATTGGGATGTCATAAGGGATAAAACYAAGACA
730 740 750 760 770 780 790 800
AAGATAGAGTCTTTGAAAGAGCATGGCCCTATCAAAAATAAAATGAGCGAAAGTCCCAATAAAACAGTATCTGAGGAAAA
810 820 830 840 850 860 870 880
AGCTAAACAATACCTAGAAGAATTTCATCAAACGGCATTAGAGCATCCTGAATTGTCAGAACTTAAAACCGTTACTGGGA
890 900 910 920 930 940 950 960
CCAATCCTGTATTCGCTGGGGCTAACTATGCGGCGTGGGCAGTAAACGTTGCGCAAGTTATCGATAGCGAAACAGCTGAT
970 980 990 1000 1010 1020 1030 1040
AATTTGGAAAAGACAACTGCTGCTCTTTCGATACTTCCTGGTATCGGTAGCGTAATGGGCATTGCAGACGGTGCCGTTCA
1050 1060 1070 1080 1090 1100 1110 1120
CCACAATACAGAAGAGATAGTGGCACAATCAATAGCTTTATCGTCTTTAATGGTTGCTCAAGCTATTCCATTGGTAGGAG
1130 1140 1150 1160 1170 1180 1190 1200
AGCTAGTTGATATTGGTTTCGCTGCATATAATTTTGTAGAGAGTATTATCAATTTATTTCAAGTAGTTCATAATTCGTAT
1210 1220 1230 1240 1250 1260 1270 1280
AATCGTCCCGCGTATTCTCCGGGGCATAAAACGCAACCATTTCTTCATGACGGGTATGCTGTCAGTTGGAACACTGTTGA
1290 1300 1310 1320 1330 1340 1350 1360
AGATTCGATAATCCGAACTGGTTTTCAAGGGGAGAGTGGGCACGACATAAAAATTACTGCTGAAAATACCCCGCTTCCAA
1370 1380 1390 1400 1410 1420 1430 1440
TCGCGGGTGTCCTACTACCGACTATTCCTGGAAAGCTGGACGTTAATAAGTCCAAGACTCATATTTCCGTAAATGGTCGG
1450 1460 1470 1480 1490 1500 1510 1520
AAAATAAGGATCGCTTGCAGAGCTATAGACGGTGATGTAACTTTTTGTCGCCCTAAATCTCCTGTTTATGTTGGTAATGG
1530 1540 1550 1560 1570 1580 1590 1600
TGTGCATGCTAACCTGTTTCGAACAGTTTCCCAATTAACAAGAGAAATTTATACAAACCCAGTATTAGAAAATTTTGATG
1610 1620 1630 1640 1650 1660 1670 1680
GTAGTTTTCGAGGCTCGGCTCAGGGCATAGAAAGAAGTATTAGGAGTCCACATTTGATGGATATACTTAACAGTATAACC
1690 1700 1710 1720 1730 1740 1750 1760
ATCTATACGGATGCTCATAGGGGTTATTATTATTGGTCAGGGCATCAAATAATGGCTTCTCCTGTAGGGTTTTCGGGGCC
1770 1780 1790 1800 1810 1820 1830 1840
AGAATTCACTTTTCCGCTATATGCAACTATGGGAAATGCAGCTCCACAACAACGTATTGTTGCTCAACTAGGTCAGGGCG
1850 1860 1870 1880 1890 1900 1910 1920
TGTATAGAACATTATCGTCCACTTTATATAGAAGACCTTTTAATATAGGGATAAATAATCAACAACTATCTGTTCTTGAC
1930 1940 1950 1960 1970 1980 1990 2000
GGGACAGAATTTGCTTATGGAACCTCCTCAAATTTCGGATCCGCTGTATACAGAAAAAGCGGAACGGTAGATTCGCTGGA
2010 2020 2030 2040 2050 2060 2070 2080
TGAAATACCGCCACAGAATAACAACGTGCCACCTAGGCAAGGATTTAGTCATCGATTAAGCCATGTTTCAATGTTTCGTT
2090 2100 2110 2120 2130 2140 2150 2160
```

-continued

```
CAGGCTTTAGTAATAGTAGTGTAAGTATAATAAGAGCTCCTATGTTCTCTTGGATACATCGTAGTGCTGAATTTAATAAT
         2170      2180      2190      2200      2210      2220      2230      2240
ATAATTGCATCGGATAGTATTACTCAAATCCCTGCAGTGAAGGGAAACTTTCTTTTTAATGGTTCTGTAATTTCAGGACC
         2250      2260      2270      2280      2290      2300      2310      2320
AGGATTTACTGGTGGGGACTTAGTTAGATTAAATAGTAGTCGAAATAACATTCAGAATAGAGGGTATATTGAAGTTCCAA
         2330      2340      2350      2360      2370      2380      2390      2400
TTCACTTCCCATCGACATCTACCAGATATCGAGTTCGTGTACGGTATGCTTCTGTAACCCCGATTCACCTCAACGTTAAT
         2410      2420      2430      2440      2450      2460      2470      2480
TGGGGTAATTCATCCATTTTTTCCAATACAGTACCAGCTACAGCTACGTCATTAGATAATCTACAATCAAGTGATTTTGG
         2490      2500      2510      2520      2530      2540      2550      2560
TTATTTTGAAAGTCGCAATGCTTTTACATCTTCATTAGGTAATATAGTAGGTGTTAGAAATTTTAGTGGGACTGCAGGAG
         2570      2580      2590      2600      2610      2620
TGATAATAGACAGATTTGAATTTATTCCAGTTACTGCAACACTCGAGTAGTAGGTCGAGAGCTT
```

FIG. 9

DNA encoding quarter-length hybrid toxin

```
         10        20        30        40        50        60        70        80
GTGAGCAGAAAACTGTTTGCGTCAATCTTAATAGGGGCGCTACTGGGGATAGGGGCCCCACCTTCAGCCCATGCAGGCGC
         90       100       110       120       130       140       150       160
TGATGATGTTGTTGATTCTTCTAAATCTTTTGTGATGGAAAACTTTTCTTCGTACCACGGGACTAAACCTGGTTATGTAG
        170       180       190       200       210       220       230       240
ATTCCATTCAAAAAGGTATACAAAAGCCAAAATCTGGTACACAAGGAAATTATGACGATGATTGGAAAGGGTTTTATAGT
        250       260       270       280       290       300       310       320
ACCGACAATAAATACGACGCTGCGGGATACTCTGTAGATAATGAAAACCCGCTCTCTGGAAAAGCTGGAGGCGTGGTGAA
        330       340       350       360       370       380       390       400
AGTGACGTATCCAGGACTGACGAAGGTTCTCGCACTAAAAGTGGATAATGCCGAAACTATTAAGAAAGAGTTAGGTTTAA
        410       420       430       440       450       460       470       480
GTCTCACTGAACCGTTGATGGAGCAAGTCGGAACGGAAGAGTTTATCAAAAGGTTCGGTGATGGTGCTTCGCGTGTAGTG
        490       500       510       520       530       540       550       560
CTCAGCCTTCCCTTCGCTGAGGGGAGTTCTAGCGTTGAATATATTAATAACTGGGAACAGGCGAAAGCGTTAAGCGTAGA
        570       580       590       600       610       620       630       640
ACTTGAGATTAATTTTGAAACCCGTGGAAAACGTGGCCAAGATGCGATGTATGAGTATATGGCTCAAGCCTGTGCAGGAA
        650       660       670       680       690       700       710       720
ATCGTGTCAGGCGATCAGTAGGTAGCTCATTGTCATGCATAAATCTTGATTGGGATGTCATAAGGGATAAAACYAAGACA
        730       740       750       760       770       780       790       800
AAGATAGAGTCTTTGAAAGAGCATGGCCCTATCAAAAATAAAATGAGCGAAAGTCCCAATAAAACAGTATCTGAGGAAAA
        810       820       830       840       850       860       870       880
AGCTAAACAATACCTAGAAGAATTTCATCAAACGGCATTAGAGCATCCTGAATTGTCAGAACTTAAAACCGTTACTGGGA
        890       900       910       920       930       940       950       960
CCAATCCTGTATTCGCTGGGGCTAACTATGCGGCGTGGGCAGTAAACGTTGCGCAAGTTATCGATAGCGAAACAGCTGAT
        970       980       990      1000      1010      1020      1030      1040
AATTTGGAAAAGACAACTGCTGCTCTTTCGATACTTCCTGGTATCGGTAGCGTAATGGGCATTGCAGACGGTGCCGTTCA
       1050      1060      1070      1080      1090      1100      1110      1120
CCACAATACAGAAGAGATAGTGGCACAATCAATAGCTTTATCGTCTTTAATGGTTGCTCAAGCTATTCCATTGGTAGGAG
       1130      1140      1150      1160      1170      1180      1190      1200
AGCTAGTTGATATTGGTTTCGCTGCATATAATTTTGTAGAGAGTATTATCAATTTATTTCAAGTAGTTCATAATTCGTAT
       1210      1220      1230      1240      1250      1260      1270      1280
AATCGTCCCGCGTATTCTCCGGGGCATAAAACGCAACCATTTCTTCATGACGGGTATGCTGTCAGTTGGAACACTGTTGA
       1290      1300      1310      1320      1330      1340      1350      1360
AGATTCGATAATCCGAACTGGTTTTCAAGGGGAGAGTGGGCACGACATAAAAATTACTGCTGAAAATACCCCGCTTCCAA
       1370      1380      1390      1400      1410      1420      1430      1440
```

-continued

```
TCGCGGGTGTCCTACTACCGACTATTCCTGGAAAGCTGGACGTTAATAAGTCCAAGACTCATATTTCCGTAAATGGTCGG
      1450      1460      1470      1480      1490      1500      1510      1520
AAAATAAGGATCGCTTGCAGAGCTATAGACGGTGATGTAACTTTTTGTCGCCCTAAATCTCCTGTTTATGTTGGTAATGG
      1530      1540      1550      1560      1570      1580      1590      1600
TGTGCATGCAGGTGCAGCTCCTATGTTCTCTTGGATACATCGTAGTGCTGAATTTAATAATATAATTGCATCGGATAGTA
      1610      1620      1630      1640      1650      1660      1670      1680
TTACTCAAATCCCTGCAGTGAAGGGAAACTTTCTTTTTAATGGTTCTGTAATTTCAGGACCAGGATTTACTGGTGGGGAC
      1690      1700      1710      1720      1730      1740      1750      1760
TTAGTTAGATTAAATAGTAGTCGAAATAACATTCAGAATAGAGGGTATATTGAAGTTCCAATTCACTTCCCATCGACATC
      1770      1780      1790      1800      1810      1820      1830      1840
TACCAGATATCGAGTTCGTGTACGGTATGCTTCTGTAACCCCGATTCACCTCAACGTTAATTGGGGTAATTCATCCATTT
      1850      1860      1870      1880      1890      1900      1910      1920
TTTCCAATACAGTACCAGCTACAGCTACGTCATTAGATAATCTACAATCAAGTGATTTTGGTTATTTTGAAAGTCGCAAT
      1930      1940      1950      1960      1970      1980      1990      2000
GCTTTTACATCTTCATTAGGTAATATAGTAGGTGTTAGAAATTTTAGTGGGACTGCAGGAGTGATAATAGACAGATTTGA
                          2010      2020      2030      2040
                ATTTATTCCAGTTACTGCAACACTCGAGTAGTAGGTCGACAGCTT
```

Amino acid sequence of half-length hybrid toxin    FIG. 10

```
  1 M S R K L F A S I L L I G A L L G I G A P P D A H A G A G G V
 31 V D S S K S F V M E N F S S Y H G T K P G Y V D S I Q K G I
 61 Q K P K S G T Q G N Y D D D W K G F Y S T D N K Y D A A G Y
 91 S V D N E N P L S G K A G G V V K V T Y P G L T K V L A L K
121 V D N A E T I K K E L G L S L T E P L M E Q V G T E E F I K
151 F R G D G A S R V V L S L P F A E G S S S V E Y I N N W E Q
181 A K A L S V E L E I N F E T R G K R G Q D A M T E Y M A Q A
211 C A G N R V R R S V G S S L S C I N L D W D V I R D K T K T
241 K I E S L K E H G P I K N K M S E S P N K T V S E E K A K Q
271 Y L E E F H Q T A L E H P E L S E L K T V T G T N P V F A G
301 A N Y A A W A V N V A Q V I D S E T A D N L E K T T A A L S
331 I L P G I G S V M G I A D G A V H N H T E E I V A Q S I A L
361 S S L M V A Q A I P L V G E L V D I G F A A Y N F V E S I I
391 N L F Q V V H N S Y N R P A Y S P G H K T Q P F L H D G Y A
421 V S W N T V E D S I I R T G F Q G E S G H D I K I T A E N T
451 P L P I A G V L L P T I P G K L D V N K S K T H I S V N G R
481 K I R M R C R A I D G D V T F C R P K S P V Y V G N G V H A
511 N L F R T V S Q L T R E I Y T N P V L E N F D G S F R G S A
541 Q G I E R S I R S P P H L M D I L N S I T I Y T D A H R G Y A Y
571 Y W S G H Q I M A S P V G F S G P E F T F P P L Y G T M G N A
601 A P Q Q R I V A Q L G Q G V Y R T L S S T L Y R R P F N I G
631 I N N Q Q L S V L D G T E F A Y G T S S N L P S A V Y R K S
661 G T V D S L D E I P P Q N N N V P P R Q G F S H R L S H V S S
691 M F R S G F S N S S V S I I R A P M F S W I H R S A E F N N
721 I I A S D S I T Q I P A V K G N F L F N G S V I S G F P G F T
751 G G D L V R L N S S G N N I Q N R G Y I E V P I H F P S T S
781 T R Y R V R V R Y A S V T P I H L N V N W G N S S I F S N T
811 V P A T A T S L D N L Q S S D F G Y F E S A N A F T S S L G
841 N I V G V R N F S G T A G V I I D R F E F I P V T A T L E
871
```

Amino acid sequence of quarter-length hybrid toxin    FIG. 11

```
  1 M S R K L F A S I L L I G A L L G I G A P P D A H A G A G G V
 31 V D S S K S F V M E N F S S Y H G T K P G Y V D S I Q K G I
 61 Q K P K S G T Q G N Y D D D W K G F Y S T D N K Y D A A G Y
 91 S V D N E N P L S G K A G G V V K V T Y P G L T K V L A L K
121 V D N A E T I K K E L G L S L T E P L M E Q V G T E E F I K
151 F R G D G A S R V V L S L P F A E G S S S V E Y I N N W E Q
181 A K A L S V E L E I N F E T R G K R G Q D A M T E Y M A Q A
211 C A G N R V R R S V G S S L S C I N L D W D V I R D K T K T
241 K I E S L K E H G P I K N K M S E S P N K T V S E E K A K Q
271 Y L E E F H Q T A L E H P E L S E L K T V T G T N P V F A G
301 A N Y A A W A V N V A Q V I D S E T A D N L E K T T A A L S
331 I L P G I G S V M G I A D G A V H N H T E E I V A Q S I A L
361 S S L M V A Q A I P L V G E L V D I G F A A Y N F V E S I I
391 N L F Q V V H N S Y N R P A Y S P G H K T Q P F L H D G Y A
421 V S W N T V E D S I I R T G F Q G E S G H D I K I T A E N T
451 P L P I A G V L L P T I P G K L D V N K S K T H I S V N G R
481 K I R M R C R A I D G D V T F C R P K S P V Y V G N G V H A
511 G A A P M F S W I H R S A E F N N I I A S D S I T Q I P A V
541 K G N F L F N G S V I S G P G F T G G D L V R L N S S G N N
571 I Q N R G Y I E V P I H F P S T S T R Y R V R V R Y A S V T
601 P I H L N V N W G N S S I F S N T V P A T A T S L D N L Q S S
631 D F G Y F E S A N A F T S S L G N I V G V R N F S G T A G
661 V I I D R F E F I P V T A T L E
691
```

The one letter symbol for the amino acids used in Figs. 10 and 11 is well known in the art. For convenience, the relationship of the three-letter abbreviation and the one letter symbol for the amino acids is as follows:

| Ala | A | Gln | Q | Leu | L | Ser | S |
| Arg | R | Glu | E | Lys | K | Thr | T |
| Asn | N | Gly | G | Met | M | Trp | W |
| Asp | D | His | H | Phe | F | Tyr | Y |
| Cys | C | Ile | I | Pro | P | Val | V |

TABLE 1

Relative molecular weights of polypeptides present in SeNPV and HzNPV LOVAL preparations as determined by SDS-polyacrylamide gel electrophoresis.

| STANDARDS | LOVAL SeNPV | HzNPV |
|---|---|---|
| 205,000 | >205,000 | |
| 97,000 | | |
| | 85,000 | 90,000 |
| | 72,000 | 76,000 |
| | | 68,000 |
| 66,000 | | |
| | 62,000 | 65,000 |

TABLE 1-continued

Relative molecular weights of polypeptides present in SeNPV and HzNPV LOVAL preparations as determined by SDS-polyacrylamide gel electrophoresis.

| STANDARDS | LOVAL SeNPV | HzNPV |
|---|---|---|
| | 55,000 | 51,000 |
| | 50,000 | 46,000 |
| 45,000 | 45,000 | 45,000 |
| | 42,000 | 40,000 |
| | | 38,000 |
| 36,000 | | |
| | 34,000 | 34,000 |

TABLE 1-continued

Relative molecular weights of polypeptides present in SeNPV and HzNPV LOVAL preparations as determined by SDS-polyacrylamide gel electrophoresis.

| | LOVAL | |
|---|---|---|
| STANDARDS | SeNPV | HzNPV |
| | 33,000 | |
| | 30,000 | 30,000 |
| 29,000 | 29,000 | |
| | 25,000 | 25,000 |
| 24,000 | <24,000 | <24,000 |

The polypeptides present in SeNPV and HzNPV LOVAL preparations were separated by polyacrylamide gel electrophoresis (7.5%) in the presence of SDS as described (Laemmli, U.K., [1970] Nature [London] 227:680–685).

TABLE 2

Hybrid virus infectivity
Number of Larvae Dead per 24 at 7 Days Post-Infection

| | VIRUS | | | |
|---|---|---|---|---|
| LARVAE | SeNPV | HzNPV | Se*HzNPV | Buffer |
| *S. exigua* | 24 | 9 | 19 | 1 |
| *H. zea* | 4 | 23 | 21 | 6 |

LOVAL was suspended in buffer containing 40 mM Trisacetate, 1 mM EDTA, pH 8.0 (TAE). Octyl glucoside was added at a ratio of 1:2 (w/w) and the mixture was incubated for 4 hours at 37° C. with constant shaking at 200 rpm. Non-solubilized viral protein was removed by centrifugation at 100,000 g for 1 hr at 4° C. The supernatant was dialyzed with HzNPV LOVAL at a ration of 1:1 (w/w) for 24 hours against 3 changes of TAE buffer. The dialysate was centrifuged at 100,000 g for 1 hr at 4° C. The supernatant was discarded and the pellet containing the hybrid virus (Se*HzNPV) was resuspended in TAE buffer to be used in bioassay or for analysis by SDS-PAGE.

TABLE 3

Relative molecular weights.

| STANDARDS | SOLUBILIZED SeNPV | HYBRID VIRUS Se*HzNPV |
|---|---|---|
| 205,000 | | |
| 97,000 | | |
| 66,000 | | |
| | 50,000 | 50,000 |
| 45,000 | | |
| | 43,000 | 43,000 |
| | 38,000 | 38,000 |
| 36,000 | | |
| 29,000 | | |
| 24,000 | | |

In order to determine which of the three polypeptides extracted by octyl glucoside solubilization of SeNPV was responsible for conferring virulence to the HzNPV hybrid virus (Se*HzNPV) to *Spodoptera exigua* the following experiment was performed: The three SeNPV proteins extracted by octyl glucoside were labeled with $^{125}I$ . The hybrid virus was prepared as described using the radiolabeled proteins and unlabeled HzNPV. An autoradiogram of an SDS-polyacrylamide gel of the hybrid virus showed all three proteins to be associated with HzNPV.

BRIEF DESCRIPTION OF THE DRAWINGS

FIGS. 1*a*–1*c*: Partial restriction endonuclease map of MR436 coding sequence.

FIG. 8*a*–8*d*: DNA encoding the half-length hybrid toxin.

FIG. 9*a*–9*c*: DNA encoding the quarter-length hybrid toxin.

FIG. 10*a*–10*b*: Amino acid sequence of the half-length hybrid toxin.

FIG. 11: Amino acid sequence of the quarter-length hybrid toxin.

DETAILED DESCRIPTION OF THE INVENTION

Figure 1C:
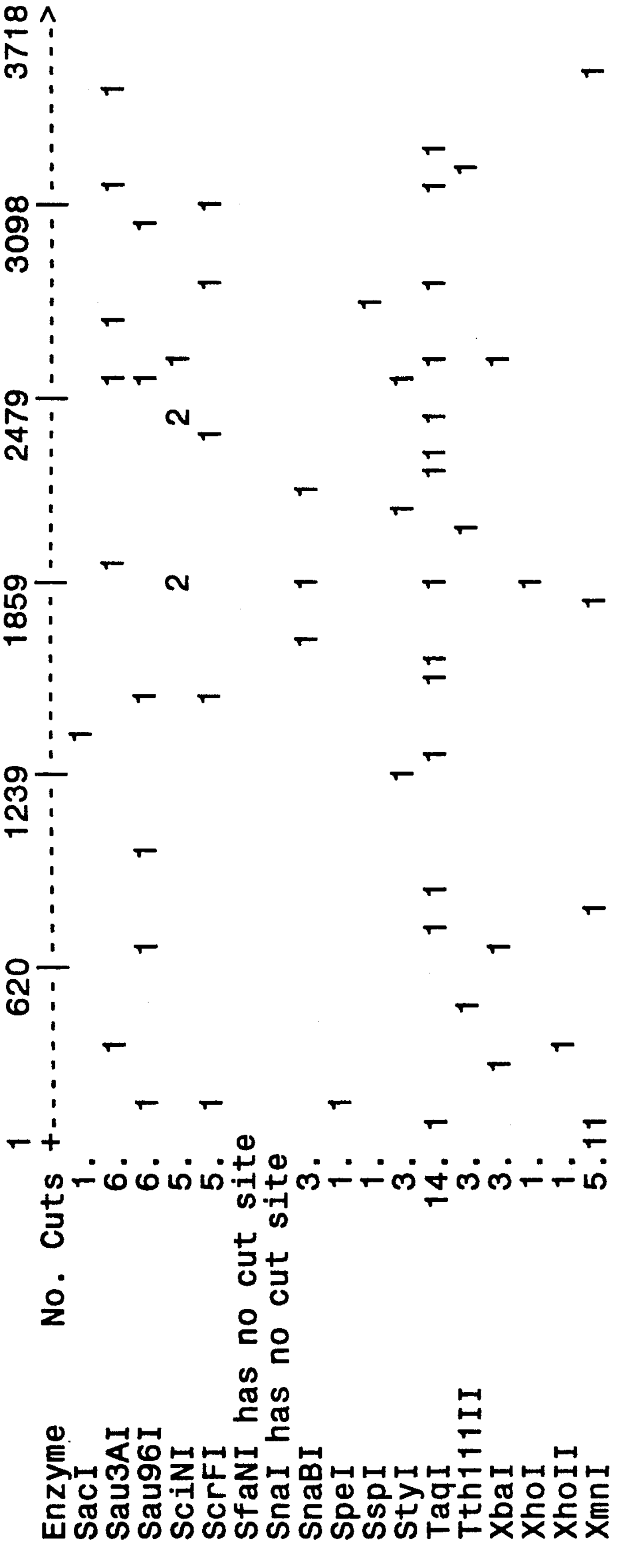

Novel hybrid toxins are produced by fusion of a pesticidal toxin to a cytotoxic agent. Specifically exemplified herein is a hybrid *B.t.* toxin prepared by fusion of the insect gut epithelial cell recognition region of a *B.t.* gene to diphtheria toxin B chain.

The hybrid toxin gene of the subject invention can be introduced into a wide variety of microbial hosts. Expression of the toxin gene results, directly or indirectly, in the intracellular production and maintenance of the pesticide. With suitable hosts, e.g., Pseudomonas, the microbes can be applied to the situs of coleopteran insects where they will proliferate and be ingested by the insects. The result is a control of the unwanted insects. Alternatively, the microbe hosting the toxin gene can be treated under conditions that prolong the activity of the toxin produced in the cell. The treated cell then can be applied to the environment of target pest(s). The resulting product retains the toxicity of the *B.t.* toxin.

Where the *B.t.* toxin gene is introduced via a suitable vector into a microbial host, and said host is applied to the environment in a living state, it is essential that certain host microbes be used. Microorganism hosts are selected which are known to occupy the "phytosphere"

(phylloplane, phyllosphere, rhizosphere, and/or rhizoplane) of one or more crops of interest. These microorganisms are selected so as to be capable of successfully competing in the particular environment (crop and other insect habitats) with the wild-type microorganisms, provide for stable maintenance and expression of the gene expressing the polypeptide pesticide, and, desirably, provide for improved protection of the pesticide from environmental degradation and inactivation.

A large number of microorganisms are known to inhabit the phylloplane (the surface of the plant leaves) and/or the rhizosphere (the soil surrounding plant roots) of a wide variety of important crops. These microorganisms include bacteria, algae, and fungi. Of particular interest are microorganisms, such as bacteria, e.g., genera Pseudomonas, Erwinia, Serratia. Klebsiella, Xanthomonas, Streptomyces, Rhizobium, Rhodopseudomonas, Methylophilius, Agrobacterium, Acetobacter, Lactobacillus, Arthrobacter, Azotobacter, Leuconostoc, and Alcaligenes; fungi, particularly yeast, e.g., genera Saccharomyces, Cryptococcus, Kluyveromyces, Sporobolomyces, Rhodotorula, and Aureobasidium. Of particular interest are such phytosphere bacterial species as *Pseudomonas syringae. Pseudomonas fluorescens, Serratia marcescens, Acetobacter xylinum, Agrobacterium tumefaciens, Rhodopseudomonas spheroides, Xanthomonas campestris, Rhizobium melioti, Alcaligenes entrophus,* and *Azotobacter vinlandii;* and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae,* and *Aureobasidium pollulans.* Of particular interest are the pigmented microorganisms.

A wide variety of ways are available for introducing the *B.t.* gene expressing the toxin into the microorganism host under conditions which allow for stable maintenance and expression of the gene. One can provide for DNA constructs which include the transcriptional and translational regulatory signals for expression of the toxin gene, the toxin gene under their regulatory control and a DNA sequence homologous with a sequence in the host organism, whereby integration will occur, and/or a replication system which is functional in the host, whereby integration or stable maintenance will occur.

The transcriptional initiation signals will include a promoter and a transcriptional initiation start site. In some instances, it may be desirable to provide for regulative expression of the toxin, where expression of the toxin will only occur after release into the environment. This can be achieved with operators or a region binding to an activator or enhancers, which are capable of induction upon a change in the physical or chemical environment of the microorganisms. For example, a temperature sensitive regulatory region may be employed, where the organisms may be grown up in the laboratory without expression of a toxin, but upon release into the environment, expression would begin. Other techniques may employ a specific nutrient medium in the laboratory, which inhibits the expression of the toxin, where the nutrient medium in the environment would allow for expression of the toxin. For translational initiation, a ribosomal binding site and an initiation codon will be present.

Various manipulations may be employed for enhancing the expression of the messenger, particularly by using an active promoter, as well as by employing sequences, which enhance the stability of the messenger RNA. The initiation and translational termination region will involve stop codon(s), a terminator region, and optionally, a polyadenylation signal.

In the direction of transcription, namely in the 5' to direction of the coding or sense sequence, the construct will involve the transcriptional regulatory region, if any, and the promoter, where the regulatory region may be either 5' or 3' of the promoter, the ribosomal binding site, the initiation codon, the structural gene having an open reading frame in phase with the initiation codon, the stop codon(s), the polyadenylation signal sequence, if any, and the terminator region. This sequence as a double strand may be used by itself for transformation of a microorganism host, but will usually be included with a DNA sequence involving a marker, where the second DNA sequence may be joined to the toxin expression construct during introduction of the DNA into the host.

By a marker is intended a structural gene which provides for selection of those hosts which have been modified or transformed. The marker will normally provide for selective advantage, for example, providing for biocide resistance, e.g., resistance to antibiotics or heavy metals; complementation, so as to provide prototropy to an auxotrophic host, or the like. Preferably, complementation is employed, so that the modified host may not only be selected, but may also be competitive in the field. One or more markers may be employed in the development of the constructs, as well as for modifying the host. The organisms may be further modified by providing for a competitive advantage against other wild-type microorganisms in the field. For example, genes expressing metal chelating agents, e.g., siderophores, may be introduced into the host along with the structural gene expressing the toxin. In this manner, the enhanced expression of a siderophore may provide for a competitive advantage for the toxin-producing host, so that it may effectively compete with the wild-type microorganisms and stably occupy a niche in the environment.

Where no functional replication system is present, the construct will also include a sequence of at least 50 basepairs (bp), preferably at least about 100 bp, and usually not more than about 1000 bp of a sequence homologous with a sequence in the host. In this way, the probability of legitimate recombination is enhanced, so that the gene will be integrated into the host and stably maintained by the host. Desirably, the toxin gene will be in close proximity to the gene providing for complementation as well as the gene providing for the competitive advantage. Therefore, in the event that a toxin gene is lost, the resulting organism will be likely to also lose the complementing gene and/or the gene providing for the competitive advantage, so that it will be unable to compete in the environment with the gene retaining the intact construct.

A large number of transcriptional regulatory regions are available from a wide variety of microorganism hosts, such as bacteria, bacteriophage, cyanobacteria, algae, fungi, and the like. Various transcriptional regulatory regions include the regions associated with the trp gene, lac gene, gal gene, the lambda left and right promoters, the Tac promoter, the naturally-occurring promoters associated with the toxin gene, where functional in the host. See for example, U.S. Pat. Nos. 4,332,898, 4,342,832 and 4,356,270. The termination region may be the termination region normally associated with the transcriptional initiation region or a different transcriptional initiation region, so long as the two regions are compatible and functional in the host.

Where stable episomal maintenance or integration is desired, a plasmid will be employed which has a replication system which is functional in the host. The replication system may be derived from the chromosome, an episomal element normally present in the host or a different host, or a replication system from a virus which is stable in the host. A large number of plasmids are available, such as pBR322, pACYC184, RSF1010, pR01614, and the like. See for example, Olson et al., (1982) J. Bacteriol. 150:6069, and Bagdasarian et al., (1981) Gene 16:237, and U.S. Pat. Nos. 4,356,270, 4,362,817, and 4,371,625.

The *B.t.* gene can be introduced between the transcriptional and translational initiation region and the transcriptional and translational termination region, so as to be under the regulatory control of the initiation region. This construct will be included in a plasmid, which will include at least one replication system, but may include more than one, where one replication system is employed for cloning during the development of the plasmid and the second replication system is necessary for functioning in the ultimate host. In addition, one or more markers may be present, which have been described previously. Where integration is desired, the plasmid will desirably include a sequence homologous with the host genome.

The transformants can be isolated in accordance with conventional ways, usually employing a selection technique, which allows for selection of the desired organism as against unmodified organisms or transferring organisms, when present. The transformants then can be tested for pesticidal activity.

Suitable host cells, where the pesticide-containing cells will be treated to prolong the activity of the toxin in the cell when the then treated cell is applied to the environment of target pest(s), may include either prokaryotes or eukaryotes, normally being limited to those cells which do not produce substances toxic to higher organisms, such as mammals. However, organisms which produce substances toxic to higher organisms could be used, where the toxin is unstable or the level of application sufficiently low as to avoid any possibility of toxicity to a mammalian host. As hosts, of particular interest will be the prokaryotes and the lower eukaryotes, such as fungi. Illustrative prokaryotes, both Gram-negative and -positive, include Enterobacteriaceae, such as Escherichia, Erwinia, Shigella, Salmonella, and Proteus; Bacillaceae; Rhizobiceae, such as Rhizobium; Spirillaceae, such as photobacterium, Zymomonas, Serratia, Aeromonas, Vibrio, Des ulfov ibrio, Spirillum; Lactobacillaceae; Pseudomonadaceae, such as Pseudomonas and Acetobacter; Azotobacteraceae and Nitrobacteraceae. Among eukaryotes are fungi, such as Phycomycetes and Ascomycetes, which includes yeast, such as Saccharomyces and Schizosaccharomyces; and Basidiomycetes yeast, such as Rhodotorula, Aureobasidium, Sporobolomyces, and the like.

Characteristics of particular interest in selecting a host cell for purposes of production include ease of introducing the *B.t.* gene into the host, availability of expression systems, efficiency of expression, stability of the pesticide in the host, and the presence of auxiliary genetic capabilities. Characteristics of interest for use as a pesticide microcapsule include protective qualities for the pesticide, such as thick cell walls, pigmentation, and intracellular packaging or formation of inclusion bodies; leaf affinity; lack of mammalian toxicity; attractiveness to pests for ingestion; ease of killing and fixing without damage to the toxin; and the like. Other considerations include ease of formulation and handling, economics, storage stability, and the like.

Host organisms of particular interest include yeast, such as Rhodotorula sp., Aureobasidium sp., Saccharomyces sp., and Sporobolomyces sp.; phylloplane organisms such as Pseudomonas sp., Erwinia sp. and Flavobacterium sp.; or such other organisms as Escherichia, Lactobacillus sp., Bacillus sp., and the like. Specific organisms include *Pseudomonas aeruginosa, Pseudomonas fluorescens, Saccharomyces cerevisiae, Bacillus thuringiensis, Escherichia coli, Bacillus subtilis,* and the like.

The cell will usually be intact and be substantially in the proliferative form when treated, rather than in a spore form, although in some instances spores may be employed.

Treatment of the microbial cell, e.g., a microbe containing the *B.t.* toxin gene, can be by chemical or physical means, or by a combination of chemical and/or physical means, so long as the technique does not deleteriously affect the properties of the toxin, nor diminish the cellular capability in protecting the toxin. Examples of chemical reagents are halogenating agents, particularly halogens of atomic no. 17–80. More particularly, iodine can be used under mild conditions and for sufficient time to achieve the desired results. Other suitable techniques include treatment with aldehydes, such as formaldehyde and glutaraldehyde; anti-infectives, such as zephiran chloride and cetylpyridinium chloride; alcohols, such as isopropyl and ethanol; various histologic fixatives, such as Bouin's fixative and Helly's fixative (See: Humason, Gretchen L., Animal Tissue Techniques, W. H. Freeman and Company, 1967); or a combination of physical (heat) and chemical agents that preserve and prolong the activity of the toxin produced in the cell when the cell is administered to the host animal. Examples of physical means are short wavelength radiation such as gamma-radiation and X-radiation, freezing, UV irradiation, lyophilization, and the like.

The cells generally will have enhanced structural stability which will enhance resistance to environmental conditions. Where the pesticide is in a proform, the method of inactivation should be selected so as not to inhibit processing of the proform to the mature form of the pesticide by the target pest pathogen. For example, formaldehyde will crosslink proteins and could inhibit processing of the proform of a polypeptide pesticide. The method of inactivation or killing retains at least a substantial portion of the bio-availability or bioactivity of the toxin.

The cellular host containing the *B.t.* insecticidal gene may be grown in any convenient nutrient medium, where the DNA construct provides a selective advantage, providing for a selective medium so that substantially all or all of the cells retain the *B.t.* gene. These cells may then be harvested in accordance with conventional ways. Alternatively, the cells can be treated prior to harvesting.

The *B.t.* cells may be formulated in a variety of ways. They may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, gels, suspensions, emulsifiable concentrates, or the like. The ingredients may include rheological agents, surfactants, emulsifiers, dispersants, or polymers.

The pesticidal concentration will vary widely depending upon the nature of the particular formulation, particularly whether it is a concentrate or to be used directly. The pesticide will be present in at least 1% by weight and may be 100% by weight. The dry formulations will have from about 1–95% by weight of the pesticide while the liquid formulations will generally be from about 1–60% by weight of the solids in the liquid phase. The formulations will generally have from about $10^2$ to about $10^4$ cells/mg. These formulations will be administered at about 50 mg (liquid or dry) to 1 kg or more per hectare.

The formulations can be applied to the environment of the coleopteran pest(s), e.g., plants, soil or water, by spraying, dusting, sprinkling, or the like.

Following are examples which illustrate procedures, including the best mode, for practicing the invention. These examples should not be construed as limiting. All percentages are by weight and all solvent mixture proportions are by volume unless otherwise noted.

EXAMPLE 1

Construction of a Hybrid Toxin Containing Near-Full Length B.t. Toxin Fused to Diphtheria Toxin B-Chain A partial restriction endonuclease map of MR436 protoxin coding sequence is depicted in FIGS. 1A and 1B. Protein coding sequences from the initiator methionine to beyond the XhoI site were derived from B.t. strain HD-73 toxin. Approximately half of the protoxin at the amino-terminal terminal end corresponds to active toxin. For HD-73, the XhoI site conveniently separates toxin and protoxin sequences. A fragment from plasmid MR436, containing nearly full-length HD-73 toxin coding sequences, was isolated by NsiI and XhoI double-digestion and gel-purification. This fragment contains amino acids (AA) $cys^{10}$ to $glu^{613}$ of HD-73 (Adang, M. J. et al. [1985] Gene 36:289–300). Plasmid pBC508 (see Murphy, J. R. et al. [1986] Proc. Nat. Acad. Sci. USA 83:8252–8262, for restriction map) which contains the B-chain of diphtheria toxin, was digested with SphI and HindIII. The SpHI site of digested, gel-purified pBC508 (minus the small SphI-HindIII fragment) was joined to the NsiI site of HD-73 DNA using a synthetic DNA oligonucleotide adaptor set:

5' - CAGGTTGCA-3'

3' - GTACGTCCA-5'

The adapters regenerate the SphI site, eliminate the NsiI site, maintain the correct translation reading frame, and add two amino acids (ala-gly) between diphtheria toxin B-chain $his^{484}$ and HD-73 $cys^{10}$. The details of the fusion junction, with the adaptors boxed, are shown below:

Gly Val His Ala Gly Cys Ile Pro

5'...GGT GTG CAT GCA GGT TGC ATT CCT...3'

3'...CCA CAC GTA CGT CCA ACG TAA GGA...5' diphtheria toxin B-chain HD-73

The XhoI site of HD-73 was joined to the HindIII site of pBC508 with a synthetic oligonucleotide adaptor set:

5' -TCGAGTAGTAGGTCGAC - 3'

3' -CATCATCCAGCTGTCGA - 5'

The adaptor set regenerates the XhoI site, adds a SalI site to the construct for use in subcloning, eliminates the HindIII site and inserts two in-frame translational termination codons. The detail of the fusion junction, with the adapters boxed, are shown below:

Thr Leu Glu term term

5'...ACA CTC GAG TAG TAG GTCGACAGCTT...3'

3'...TGT GAG CTC ATC ATC CAGCTGTCGAA...5'

HD-73 pBC508

The correct construct was identified by restriction enzyme analysis. HD-73 coding sequence was confirmed by the presence of unique SstI and AsuII sites. The SphI site was regenerated and a SalI site created, confirming presence of linkers. Digestion with EcoRI confirmed correct orientation of HD-73 coding sequence with respect to the diphtheria toxin B-chain. Finally, combinations of enzymes which cut the hybrid toxin construct (designated p26) at a fusion junction and/or internally gave DNA fragments which comigrated with fragments generated by equivalent digests of MR436 (NRRL B-18292), within limits of resolution of the gel system are shown below:

| p26 | MR436 |
|---|---|
| SphI × SalI | NsiI × XhoI |
| SphI × XhoI | NsiI × XhoI |
| SphI × AsuII | NsiI × AsuII |
| SphI × SstI | NsiI × SstI |
| SstI × XhoI | SstI × XhoI |
| AsuII × XhoI | AsuII × XhoI |

The correct translational reading frame at the fusion junction between diphtheria toxin B-chain and HD-73 coding sequences was verified by dideoxy DNA sequencing of p26 using a synthetic oligonucleotide primer corresponding to nucleotides 500 to 523 of the diphtheria toxin gene (Murphy, J. R. [1985] Current Topics Microbiol. Immunol. 118:235–251):

5' - GACGGTGATGTAACTTTTTGTCGC - 3'

EXAMPLE 2

Construction of Hybrid Toxin Clones Containing Shorter Lengths of HD-73 Coding Sequence Fused to Diphtheria Toxin B-Chain Plasmid p26, described above, served as the substrate for additional hybrid toxin constructions. Two constructs were generated which either fuse His$^{484}$ of diphtheria toxin B-chain to amino acids Arg$^{258}$ through Glu$^{613}$ of HD-73 (plasmid construct p151), or His$^{484}$ of diphtheria toxin B-chain to amino acid Ala$^{450}$ through Glu$^{613}$ of HD-73 (plasmid construct p11). Hybrid toxin plasmid p151 was generated by restriction digestion of p26 with SphI and AsuII, gel-purification of the DNA fragment containing pBC508 plus HD-73 coding for Arg$^{258}$ through the synthetic XhoI-HindIII adaptor (described above), and re-ligation of the SphI to the AsuII site with a synthetic oligonucleotide adaptor set of the sequence:

5' - CTAACCTGTTT -3'

3' - GTACGATTGGACAAAGC 5'

The adaptor set regenerates the SphI and AsuII sites, maintains the correct translational reading frame, and inserts four amino acids (Ala-Asn-Leu-Phe) between His$^{484}$ of the diphtheria toxin B-chain and Arg$^{258}$ of HD-73 coding sequence. Details of the predicted construct at the fusion junction, with the synthetic adapters boxed, are shown below:

```
        Gly  Val  His  Ala   Asn  Leu  Phe  Arg   Thr
5'...GGT  GTG  CAT  G|CT  AAC  CTG  TTT |CGA  ACA...3'
3'...CCA  CAC |GTA  CGA   TTG  GAC  AAA  GC|T  TGT...5'

diphtheria toxin                         HD-73
B-chain
```

Recombinant plasmids were screened for the presence of the SphI site, and the correct size of the insert was demonstrated by agarose gel-sizing of EcoRI digested p26 and p151, and by double-digests comparing p26 (AsuII×SalI) with p151 (SphI×SalI).

Correct translational reading frame at the fusion junction was verified by dideoxy DNA sequencing of p151 with the synthetic sequencing primer used for p26 (above) and with a second synthetic oligonucleotide sequencing primer which corresponds to nucleotides 479 to 499 of the diphtheria toxin structural gene (Murphy, J. R. [1985] supra):

5' - AGGATGCGTTGCAGAGCTATA - 3'

Hybrid toxin plasmid p11 was constructed by restriction digestion of p26 with SphI and SstI, gel-purification of the DNA fragment containing pBC508 plus HD-73 coding for Ala$^{450}$ through the synthetic XhoI-HindIII adaptor (described above), and re-ligation of the SphI to the SstI site with a synthetic oligonucleotide adaptor set.

5' - CAGGTGCAGCT - 3'

3' - GTACGTCCACG - 5'

The adaptor set regenerates the SphI site, eliminates the SstI site, maintains the correct translational reading frame, and inserts three amino acids (Ala-Gly-Ala) between His$^{484}$ of the diphtheria toxin B-chain and Ala$^{450}$ of the HD-73 coding sequence. Detail of the predicted structure at the fusion junction, with synthetic oligonucleotides boxed are shown below:

```
        Gly  Val  His  Ala   Gly  Ala  Ala   Pro   7
5'...GGT  GTG  CAT  G|CA  GGT  GCA  GCT|  CCT...3'
3'...CCA  CAC |GTA  CGT   CCA  CG|T  CGA   GGA...5'

diphtheria                          HD-73
toxin B-chain
```

Recombinant plasmids were screened for the presence of the SphI site, and the correct size of the insert was demonstrated by agarose gel-sizing of EcoRI digests of p11 compared to p26, and by multi-enzyme digests comparing p11 with p26 as follows:

| p26 | p11 |
|---|---|
| SphI × SalI × SstI | SphI × SalI |
| SstI × SalI | SphI × SalI |

Correct translational reading frame at the fusion junction was demonstrated by dideoxy DNA sequencing of p11 with the same two synthetic oligonucleotide primers used for p151.

EXAMPLE 3

Construction of Hybrid Toxin Expression Vectors Containing Fused Coding Sequences for Diphtheria Toxin A-Chain and Truncated B-Chain and HD-73

HD-73 coding sequence DNA fragments were excised from plasmids p26, p151, and p11 by digestion with SphI and SalI, and gel-purified. These gel-purified fragments were used for construction of a hybrid toxin expression vector containing diphtheria toxin A and B-chains and HD-73 coding sequences. Assembly of the hybrid toxin expression vector was done under BL-3 containment conditions. Plasmid pABI508 was digested with SphI and SalI to remove interleukin-2 (IL-2) coding sequence DNA. The vector (minus IL-2) was gel-purified. Purified SphI×SalI HD-73 inserts were ligated separately to the purified SphI×SalI pABI508 vector DNA. The ligation mixes were used to transform E. coli strain SY327 cells. Correctly assembled hybrid toxin plasmids were identified with Western blots by their ability to produce anti-HD-73 immunoreactive material under control of the constitutively utilized ptox promoter of the diphtheria toxin gene. Synthesis of three size classes of immunoreactive material was detected. A hybrid toxin made with p26 SphI×SalI HD-73 DNA gave immunoreactive protein which migrated between the 116 kd and 180 kd protein standards (computer-generated molecular weight is about 126 kd). A hybrid toxin made with the p151 SphI×SalI HD-73 insert gave immunoreactive protein which migrated between the 84 kd and 116 kd protein standards (computer-predicted molecular weight is about 98 kd). A hybrid toxin made with the p11 SphI×SalI HD-73 insert DNA gave an immunoreactive protein which migrated between the 58 kd and 84 kd protein standards (computer-predicted molecular weight is about 76 kd).

EXAMPLE 4

Expression of Hybrid Toxins in E. coli

Under BL-3 containment conditions, E. coli cells were grown in LB medium (with or without ampicillin) overnight at 30° C. Cells were collected by centrifugation and treated by one of the following three methods:

(a) Whole cells were killed with ultraviolet irradiation and kept on ice.

(b) Periplasmic protein extracts were prepared from whole cells. Cell pellets were resuspended in ice-cold buffer containing 20% sucrose/10 mM Tris-HCl, pH 8.0, 1 mM ethylenediaminetetraacetic acid (EDTA). A volume of cold buffer containing 1.5 mg/ml lysozyme, equal in volume to the volume used for resuspension, was added and incubation proceeded for 20 minutes at 4° C. Cells were removed by centrifugation and the supernatant containing the periplasmic proteins was sonicated and filtered through 0.45 μM filters. Filtered extract was frozen. The majority of hybrid toxin molecules in this extract should lack the diphtheria toxin leader sequence (amino acids −1 to −25) (Murphy [1985] supra) which should be clipped during secretion into the periplasmic space (Murphy, John R., U.S. Pat. No. 4,675,382).

(c) Whole-cell extracts were prepared by disruption with a French Press (French pressure cell-laboratory hydraulic press) as follows. Cell pellets were resuspended in ice-cold buffer containing 20% glycerol/50 mM Tris-HCl, pH 7.4/1 mM EDTA/1 mM dithiothreitol (DTT)/approximately 1 mM phenylmethylsulfonyl fluoride (PMSF). Cells were disrupted twice with the French Press at 12,000 to 14,000 psi. Cell extracts were frozen. The hybrid toxins should be a mixed population of molecules with respect to the presence of the diphtheria toxin leader sequence (amino acids −1 to −25) since some molecules were likely not secreted.

EXAMPLE 5

Purification of Hybrid Toxin

An immunoadsorbent resin was constructed by coupling an equine polyclonal diphtheria toxin antibody (Connaught Laboratories, Swiftwater, Pa.) to cyanogen bromide (CNBr)-activated SEPHAROSE™ 4B (Pharmacia Fine Chemicals, Piscataway, N.J.) by following the latter manufacturer's procedure. Briefly, 3 g of lyophilized CNBr-activated SEPHAROSE™ was cycled into and repeatedly washed with 1 mM HCl. The resulting swollen gel was then washed with coupling buffer (0.5M NaCl and 0.1M $NaHCO_3$, pH 8.3). An aliquot of the diphtheria toxin antibody corresponding to 60 mg was suspended in coupling buffer at a final concentration of 5 mg protein to 5 ml buffer. The SEPHAROSE™ and antibody solution were then combined and allowed to incubate at room temperature for 2 hours with end over end mixing. Following the incubation period, the resin was briefly centrifuged (1000 xg ×15 min) and the supernatant was removed. Residual unoccupied reactive groups on the resin matrix were blocked by the addition of 0.2M glycine, pH 8.0 and allowing to incubate as before. Finally, the immunoadsorbent was washed sequentially in high and low pH buffers (coupling buffer and a buffer comprised of 0.1M NaCl and 0.1M $NaHCO_3$, pH 4). This wash was repeated 4 times to ensure that ionically bound free ligand was removed. This procedure resulted in an overall coupling efficiency of 95%. The prepared immunoadsorbent contained 5.7 mg ligand per ml resin. The immunosorbent was pre-equilibrated with loading buffer (100 mM Tris-Cl, pH 7.4, 20% glycerol, 1 mM $Na_2EDTA$, 1 mM PMSF, 0.1% nonidet P-40 (NP-40) and 0.1 mM DTT) at 4° C. prior to chromatography.

All of the following steps were performed at 4° C. unless otherwise noted. The disrupted cell pellet containing the hybrid toxin was partially solubilized by the addition of NP-40 to a final concentration of 0.1% (v/v) to promote dissolution of hydrophobic aggregates. An aliquot of the partially solubilized material, corresponding to 50 mg total protein, was incubated with a slurry of the resin corresponding to 0.5 ml SEPHAROSE™ for 3 hr with end over end mixing. Non-specifically bound material was removed from the resin by repeatedly cycling it into wash buffer (100 mM Tris-Cl, pH 7.4, 20% glycerol, 0.2% NP-40 and 0.1% cholic acid). This was followed by successive washes in 0.1M Tris-Cl to remove all traces of detergent. Finally, the hybrid toxin was eluted by a short incubation with 4M guanidine-HCl in 0.1M Tris-Cl, pH 7.4. This fraction was then dialyzed exhaustively against a buffer containing 20 mM Tris-Cl, pH 7.4, 0.1M NaCl and 0.25 mM reduced glutathione to promote proper refolding.

EXAMPLE 6

Insertion of Toxin Gene Into Plants

The novel genes coding for the novel insecticidal toxins, as disclosed herein, can be inserted into plant cells using the Ti plasmid from *Agrobacter tumefaciens.* Plant cells can then be caused to regenerate into plants (Zambryski, P., Joos, H., Gentello, C., Leemans, J., Van Montague, M. and Schell, J [1983] Cell 32:1033-1043). A particularly useful vector in this regard is pEND4K (Klee, H. J., Yanofsky, M. F. and Nester, E. W. [1985] Bio/Technology 3:637-642). This plasmid can replicate both in plant cells and in bacteria and has multiple cloning sites for passenger genes. The toxin gene, for example, can be inserted into the BamHI site of pEND4K, propagated in E. coli, and transformed into appropriate plant cells.

EXAMPLE 7

Cloning of Novel *B. thuringiensis* Genes Into Baculoviruses

The novel genes of the invention can be cloned into baculoviruses such as *Autographa californica* nuclear polyhedrosis virus (AcNPV). Plasmids can be constructed that contain the AcNPV genome cloned into a commercial cloning vector such as pUC8. The AcNPV genome is modified so that the coding region of the polyhedrin gene is removed and a unique cloning site for a passenger gene is placed directly behind the polyhedrin promoter. Examples of such vectors are pGP-B6874, described by Pennock et al. (Pennock, G. D., Shoemaker, C. and Miller, L. K. [1984] Mol. Cell. Biol. 4:399–406), and pAC380, described by Smith et al. (Smith, G. E., Summers, M. D. and Fraser, M. J. [1983] Mol Cell. Biol. 3:2156–2165). The gene coding for the novel protein toxin of the invention can be modified with BamHI linkers at appropriate regions both upstream and downstream from the coding region and inserted into the passenger site of one of the AcNPV vectors. Other baculoviruses can be used, e.g., *Spodoptera exigua* nuclear polyhedrosis virus (SeNPV) and *Heliothis zea* nuclear polyhedrosis virus (HzNPV). Each of these viruses is specific for its own host with little activity for other insects (i.e., SeNPV will infect *Spodoptera exigua* but not *Heliothis zea,* and vice versa).

EXAMPLE 8

Propagation of Viruses

The viruses are propagated by infecting the appropriate larvae. This can be accomplished by direct application of inoculum to the surface of diet cups and placing fourth instar larvae on the diet as described by Maruniak (Maruniak, J. E. [1986] The Biology of Baculoviruses, Vol. 1, pp. 129–1;75, R. R. Granados and B. A. Federici, eds., CRC Press). Larvae are then harvested at six days post infection and NPV isolated as follows. The larvae are collected, homogenized and filtered through cheesecloth. The filtrate is then centrifuged for 15 minutes at 8,000 xg. The resulting pellet is resuspended in buffer that contains 0.01M Tris-HCl pH 7.8 and 1.0 mM EDTA, (TE buffer). The suspension is layered onto a 20–90% sucrose gradient and centrifuged for 60 min at 100,000 xg. The polyhedra, localized as a defined band at approximately 60%, is removed and diluted in TE buffer. The polyhedra are then isolated by centrifugation for 30 min at 10,000 xg.

The purified polyhedral pellet is resuspended in TE buffer and alkali extracted with an equal volume of 0.2M $Na_2CO_3$ pH 10.9, 0.17M NaCl, and 1.0 mM EDTA. The extraction is allowed to proceed for 60 min at room temperature with continuous mixing. The larval occluded virus alkali liberated or LOVAL are isolated by centrifugation and a 20–90% sucrose at 100,000 xg for 60 min. These represent single, double or multiply embedded virions. All bands are recovered, diluted into TE buffer and centrifuged at 100,000 xg for 60 min. The resulting pellet is resuspended in TE buffer containing 1.0 mM PMSF.

The polypeptide components of the SeNPV and HzNPV LOVAL fractions are analyzed by polyacrylamide gel electrophoresis (PAGE) in the presence of sodium dodecyl sulfate (SDS) by the method of Laemmli (Laemmli, U.K., [1970] Nature [London] 227:680–685). The molecular weights determined from the relative electrophoretic mobilities are shown in Table 5. Following the above procedures, we identified thirteen and fourteen polypeptides for the HzNPV and SeNPV LOVAL preparations, respectively.

A bioassay of these preparations demonstrated minimal infectivity of the SeNPV LOVAL in *Heliothis zea* larvae. The converse was also found to be true; the infectivity of HzNPV LOVAL in *Spodoptera exigua* was limited.

EXAMPLE 9

Construction of Hybrid Virus

Virulence/specificity of baculoviruses is conferred by fusogen components in the virion envelope. Using known techniques for alteration of the target recognition of Epstein-Barr virus with re-associated Sendai virus envelopes (Shapiro, I. M. et al. [1982] Science 219:1225–1228; Volsky, D. J. et al. [1980] Proc. Natl. Acad. Sci. U.S.A. 77:5453–5457; Volsky, D. J. et al. [1979] Proc. Natl. Acad. Sci. U.S.A. 76:5440–5444) we constructed a hybrid virus by re-associating solubilized envelope proteins from SeNPV LOVAL with HzNPV. The procedure involved suspending the LOVAL fraction in 40 mM Tris-acetate pH 8.0 containing 1.0 mM EDTA (TAE buffer). This suspension was incubated with octyl glucoside 1:2 (w/w) at 37° C. for 4 hr with continuous shaking. Insoluble proteins were removed by centrifugation for 60 min at 100,000 xg. The supernatant containing the solubilized viral proteins was combined with purified HzNPV LOVAL 1:1 (w/w). The detergent was removed by dialysis at 4° C. for 24 hr with 3 changes of TAE buffer. The hybrid virus was isolated by centrifugation for 60 min at 100,000 xg through a 10% sucrose cushion.

The resultant hybrid virus was then used to infect both *Spodoptera exigua* and *Heliothis zea* larvae. The results of this study are reported in Table 6. These data show that the hybrid HzNPV has activity against *Spodoptera exiqua* that HzNPV does not.

To determine which polypeptide(s) were responsible for conferring virulence, the octyl glucoside extract of SeNPV LOVAL was radiolabeled with $^{125}I$ and combined with unlabeled HzNPV LOVAL. An autoradiogram of the SDS-PAGE of the octyl glucoside extract SeNPV showed three polypeptides present in the soluble fraction. Similar analysis of the hybrid virus showed all three SeNPV proteins to be associated with the HzNPV hybrid. The relative molecular weights of these polypeptides as determined by electrophoretic mobility are shown in Table 7.

We have demonstrated an alteration of NPV host range following construction of a hybrid virus. We conclude that one of the proteins contained in the octyl glucoside extract confers virulence for *Spodoptera exigua* to HzNPV. Thus, we have demonstrated that it is possible to confer virulence from one occluded NPV to another through re-association of envelope proteins.

EXAMPLE 10

Construction of a Hybrid Toxin Using NPV Fusogenic Protein to Replace *Bacillus thuringiensis* Recognition Protein Construction of the hybrid virus demonstrates that the proteins in the envelope of the NPV are responsible for altering the virulence. We have identified the three putative proteins involved with this recognition and purified them for determination of individual contribution to the recognition event necessary for the observed alteration in virulence. This determination can be accomplished by constructing three different hybrid viruses with the three individual purified proteins isolated from octylglucoside fraction and HzNPV, as previously described. These are bioassayed individually to determine which hybrid virus confers virulence. The protein responsible for recognition so identified can be purified and the amino acid sequence determined from reverse phase HPLC purified tryptic fragments of the protein. The amino acid sequence can be used to construct oligonucleotide probes which can be used to identify and isolate the gene that codes for the recognition fusogen from a gene library that is made to the viral DNA by standard molecular genetic techniques. The identified and isolated DNA then can be sequenced to define the open reading frame that codes for the protein. The DNA coding for the recognition fusogen can be cloned into the hybrid toxin construct in place of the B. thuringiensis recognition sequence using techniques described frequently.

It is well known in the art that the amino acid sequence of a protein is determined by the nucleotide sequence of the DNA. Because of the redundancy of the genetic code, i.e., more than one coding nucleotide triplet (codon) can be used for most of the amino acids used to make proteins, different nucleotide sequences can code for a particular amino acid. Thus, the genetic code can be depicted as follows:

Phenylalanine (Phe)
Leucine (Leu) XTY
Isoleucine (Ile) ATM
Methionine (Met) ATG
Valine (Val) GTL
Serine (Ser)
Histidine (His) CAK
Glutamine (Gln) CAJ
Asparagine (Asn) AAK
Lysine (Lys) AAJ
Aspartic acid (Asp) GAK
Glutamic acid (Glu) GAJ
Proline (Pro) CCL
Threonine (Thr) ACL
Alanine (Ala) GCL
Tyrosine (Tyr) TAK
Termination signal TAJ
Cysteine (Cys) TGK
Tryptophan (Trp) TGG
Arginine (Arg) WGZ
Glycine (Gly) GGL Key: Each 3-letter deoxynucleotide triplet corresponds to a trinucleotide of mRNA, having a 5'-end on the left and a 3'-end on the right. All DNA sequences given herein are those of the strand whose sequence correspond to the mRNA sequence, with thymine substituted for uracil. The letters stand for the purine or pyrimidine bases forming the deoxynucleotide sequence.

A=adenine
G=guanine
C=cytosine
T=thymine
X=T or C if Y is A or G
X=C if Y is C or T
Y=A, G, C or T if X is C
Y=A or G if X is T
W=C or A if Z is A or G
W=C if Z is C or T
Z=A, G, C or T if W is C
Z=A or G if W is A
QR=TC if S is A, G, C or T; alternatively QR=AG if S is T or C
J=A or G
K=T or C
L=A, T, C or G
M=A, C or T The above shows that the novel amino acid sequence of the *B.t.* toxin can be prepared by equivalent nucleotide sequences encoding the same amino acid sequence of the protein. Accordingly, the subject invention includes such equivalent nucleotide sequences. In addition it has been shown that proteins of identified structure and function may be constructed by changing the amino acid sequence if such changes do not alter the protein secondary structure (Kaiser, E. T. and Kezdy, F. J. [1984] Science 223:249-255). Thus, the subject invention includes mutants of the amino acid sequence depicted herein which do not alter the protein secondary structure, or if the structure is altered, the biological activity is retained to some degree.

MATERIALS AND METHODS USED IN THE BIOCHEMICAL ANALYSIS OF HYBRID TOXINS

Materials

The CF-1 cell line, derived from *Choristoneura fumiferana,* was obtained from the Canadian Forestry Research Laboratories (Dr. S. Sohi, Sault Ste. Marie, Ont., Canada). Nicked diphtheria toxin was purchased from Calbiochem (San Diego, Calif.), and radioisotopes ($^{14}$C-leucine and $^{14}$C-NAD) from DuPont/NEN (Boston, Mass.) at specific activities of 308 and 600 respectively. HD-73 *Bacillus thuringiensis* toxin crystals were isolated by NaBr gradient centrifugation. All other chemicals and reagents were of the highest commercially available purity.

METHODS

Cell Culture

CF-1 cell culture stocks were maintained at 28° C. in 75 cm$^2$ T-flasks with Grace's insect medium (GIBCO, Compton, Calif.) supplemented with 10% fetal bovine serum, 2 mM L-Glutamine and 2.7 gm/l tryptose broth powder (DIFCO, Detroit, Mich.). Cultures were passaged daily by 1:1 splits.

Radioiodination

The 64 kd toxic component of HD-73 was produced by digestion of HD-73 crystals (1 mg/ml) dissolved in 50 mM CAPS buffer (pH 11) with trypsin (0.1 mg/ml). Digestions were conducted at 37° C. on a shaker bath for 3 hr, followed by dialysis against a 20 mM glycine-Tris buffer (pH 8.5). Radioiodinations were conducted in a reaction mix comprised of 100 μg toxin, 50 μg chloramine-T, 1 mCi of Na$^{125}$I and sufficient volume of 100 mM NaPi buffer, pH 7.0 to give a 1.0 ml final volume. The mixture was reacted at 4° C. for 5 minutes, the subjected to centrifugal filtration (Centricon, by Amicon; Danvers, Mass.) to remove unbound $^{125}$I.

Cyanogen Bromide Digestions

To 7 mg of HD-73 64 kd toxin was added 8 ml of 88% formic acid and 212 mg of CNBr. The mixture was reacted for 24 hr at 25° C. in the dark, then dialyzed against five 2-1 changes of 20 mM glycine-Tris buffer, pH 8.6.

Binding Assays

CF-1 cells were harvested by centrifugation and resuspended at a concentration of 2.94×10$^5$/ml in Tyrode's solution (in gm/l: NaCl, 7.0; $CaCl_2.2H_2O$, 0.2; $NaH_2PO_4$, 0.2; KCl, 0.2; $MgCl_2.6H_2O$, 0.1; HEPES, 4.8; glucose, 8.0; pH 6.3) containing 1 mg/ml bovine serum albumin. For binding assays, 450 μl of cell suspension was incubated with 50 μl of unlabeled toxin or CNBr digest at various concentrations for 20 min at 25° C., then with 25 μl of iodinated toxin for an additional 20 min. The cells were then recovered and washed (3×5 ml of 50 mM CAPS buffer, pH 11) by vacuum filtration on Whatman GF/A filter discs, and cell-bound radioactivity was quantitated by liquid scintillation. Control binding was determined as described above but in the absence of competing ligand. Background binding to the filter discs was determined from incubations performed in the absence of cells.

EF-2 Ribosylation Assays

Elongation factor 2 (EF-2) was extracted from raw wheat germ and partially purified as previously described (Legocki, A. B. [1979] Methods Enzymol. 50:703-712). $^{14}$C-NAD was diluted to a specific activity of 240 mCi/mmol with deionized water. Ribosylation assays were performed in a final volume of 200 μl containing 170 μl of EF-2 (0.8 mg), 20 μl of hybrid toxin or diphtheria toxin (control) and 10 μl of $^{14}$C-NAD. Toxin and EF-2 were incubated at 37° C. for 20 minutes, followed by the addition of $^{14}$C-NAD and subsequent incubation for 30 minutes at 37° C. The reaction was stopped by the addition of 3 ml of ice-cold 5% trichloroacetic acid (TCA), and the precipitated protein was collected by vacuum filtration on GF/A filter discs, which were counted by liquid scintillation.

$^{14}$C-Leucine Incorporation into Protein in CF-1 Cells

Incubations were typically conducted in a volume of 500 μl containing 450 μl of CF-1 cells suspended in cell medium at a concentration of $5\times10^6$/ml and 50 μl of hybrid toxin, diphtheria toxin, HD-73 or appropriate buffer control. At varying intervals, 100 μl aliquots were withdrawn and incubated with 10 μl of $^{14}$C-leucine for 30 min. Cells were pelleted by centrifugation, discarding the supernatant. The cell pellet was solubilized by the addition of 200 μl of 0.1N KOH, and protein was precipitated by the addition of 200 μl of ice-cold 20% TCA. After 15 min on ice, the TCA precipitate was collected by vacuum filtration on Whatman GF/B discs (Whatman Laboratory Products, Clifton, N.J.) and washed twice with 3 ml of cold 10% TCA. Filter discs were counted for radioactivity as described elsewhere.

Figure 2:
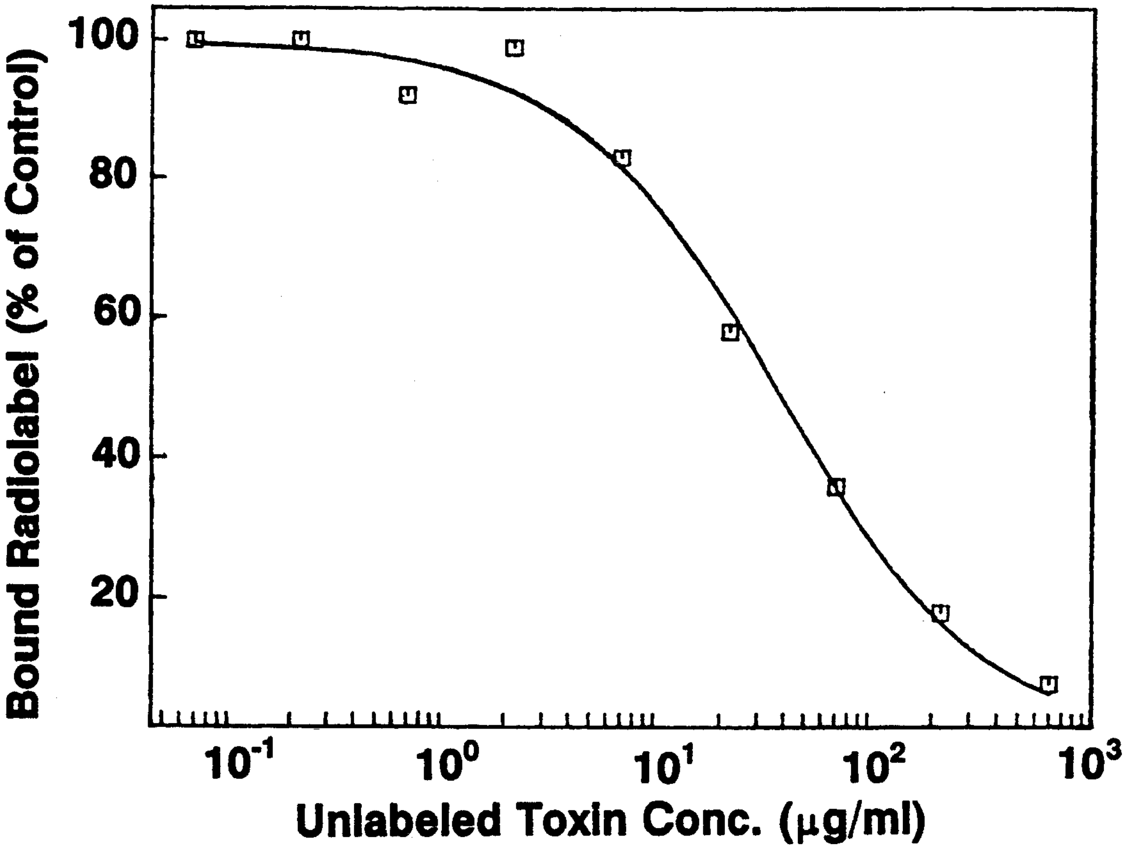
FIG. 2: HD-73 toxin binding to CF-1 cells. Cells were incubated with the indicated concentrations of unlabeled HD-73 for 20 minutes, then with radioiodinated toxin for an additional 30 minutes. Bound radioactivity was determined as described in Materials and Methods.

Autoradiograms developed from SDS-PAGE gels of radioiodinated HD-73 demonstrated labeling of the 64 kd active toxin protein produced by trypsin digestion. The specific activity of labeling was estimated to be $3\times10^{16}$ cpm/mol. FIG. 2 shows that unlabeled HD-73 competes with the labeled toxin for binding to CF-1 cells with an $IC_{50}$ of 35 μg/ml. In addition, binding of radiolabeled toxin equilibrated rapidly (<5 min), and was not reversed by wash out procedures. Saturation studies gave an estimate of $>1\times10^6$ binding sites per cell. These findings demonstrate specific binding of the radiolabeled 64 kd tryptic peptide of HD-73 to CF-1 insect cells in culture. The 64 kd component is therefore considered a viable candidate for the binding site recognition portion of a hybrid toxin construct.

Figure 3:
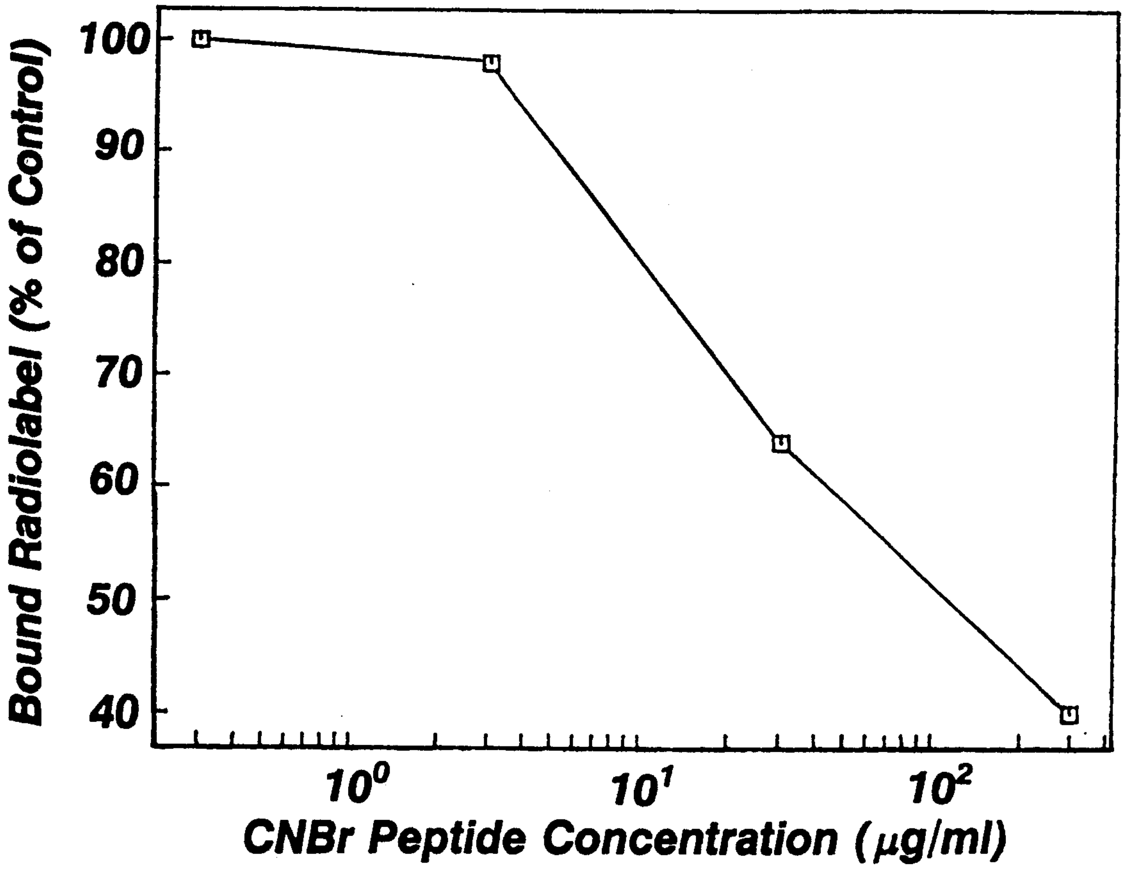
FIG. 3: CNBr peptide competition with radioiodinated HD-73 for binding to CF-1 cells. HD-73 toxin was digested with CNBr and dialyzed. CF-1 cells were incubated with the indicated concentrations of the digest peptides for 20 minutes, then with radioiodinated HD-73 toxin for an additional 30 minutes. Bound radioactivity was determined as described in Materials and Methods.

In order to further delineate the binding site recognition domain of the 64 kd toxin, CNBr digestions were performed to generate smaller peptides for analysis. Following dialysis through a 14 kd cutoff membrane, we obtained peptides of 18 and 19 kd molecular weights as evidenced by SDS-PAGE. Binding experiments with CF-1 cells demonstrated that this peptide mixture partially competes for iodinated 64 kd binding (FIG. 3). It is therefore likely that the binding domain of HD-73 can be mapped to at least one of these two CNBr-generated peptides.

Figure 4:
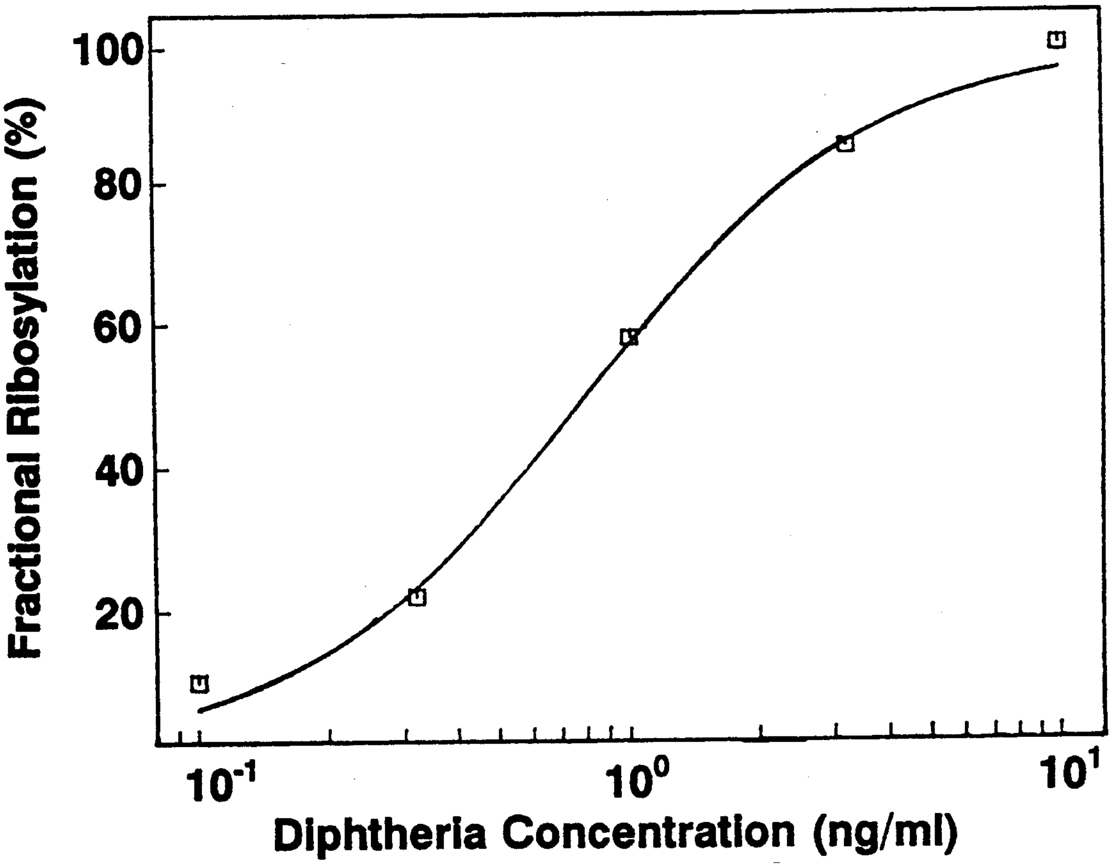
FIG. 4: Diphtheria toxin-catalyzed ADP-Ribosylation of EF-2. Partially purified EF-2 from wheat germ was incubated with the indicated concentrations of diphtheria toxin for 10 minutes, then with $^{14}C$-NAD for an additional 30 minutes at 37° C. The reaction was terminated by the addition of cold TCA, and the precipitated protein was recovered and counted for radioactivity as described in Materials and Methods. The extents of ribosylation are .expressed as a percentage of that obtained with saturating concentrations of diphtheria toxin.
Figure 5:
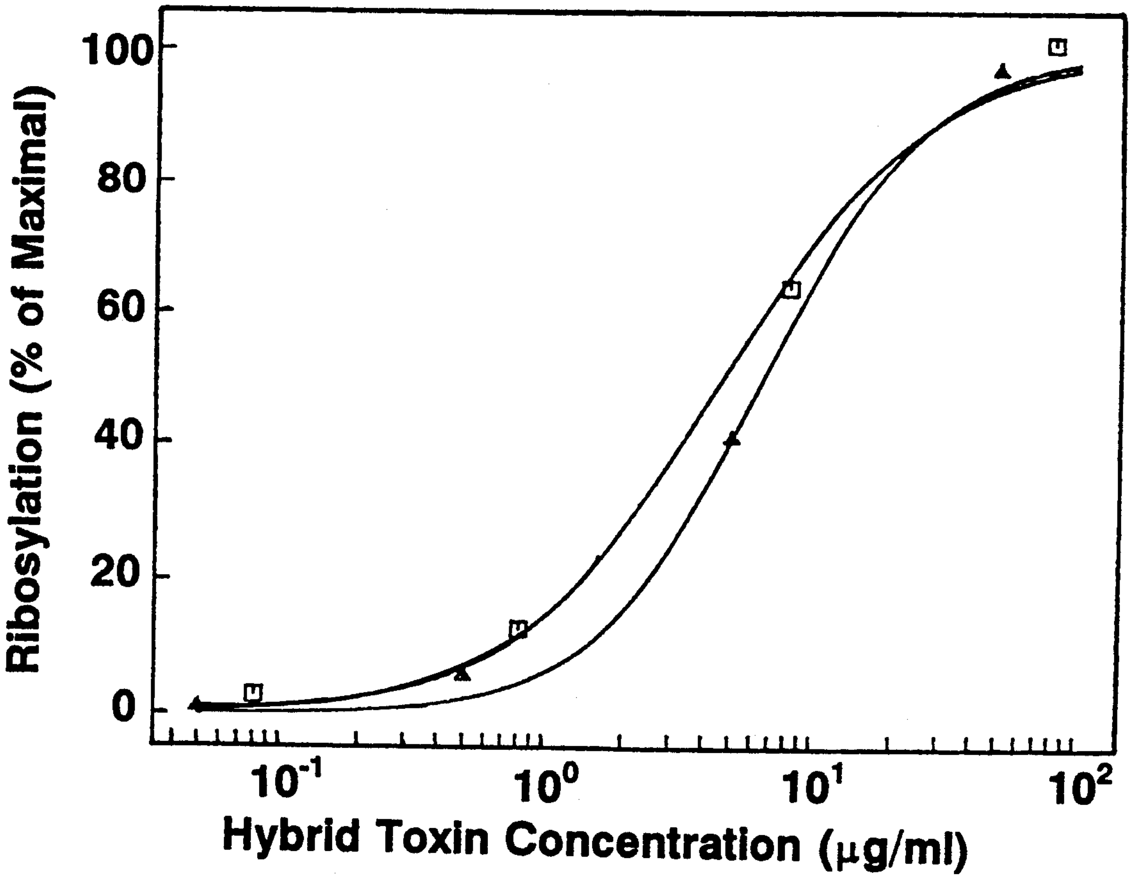
FIG. 5: Hybrid toxin-catalyzed ribosylation of EF-2. Wheat germ EF-2 was incubated with quarter (□) or half length (▲) hybrid toxins at the indicated concentrations for 10 minutes, then with $^{14}C$-NAD for 30 minutes. Samples were processed as described for FIG. 3. Ribosylation is expressed as a percentage of that obtained with a saturating concentration of diphtheria toxin.

FIG. 4 gives the concentration dependence for diphtheria toxin—stimulated ADP—ribosylation of wheat germ EF-2. Half maximal ribosylation was obtained at a diphtheria toxin concentration of 0.8 ng/ml. The extent of ADP-ribosylation at saturating diphtheria toxin concentrations was quite reproducible in our hands, and was therefore used as an index for quantitating hybrid toxin-catalyzed ribosylation. FIG. 5 gives the results for such determinations, showing that quarter- and half-length hybrid toxins are roughly equivalent with respect to their ribosylation capacities, though 5000-fold less potent than diphtheria toxin. However, uncertainty in the relative purity of the hybrid toxin preparation makes the latter comparison approximate, and almost certainly represents a low end estimate of potency.

Figure 6:
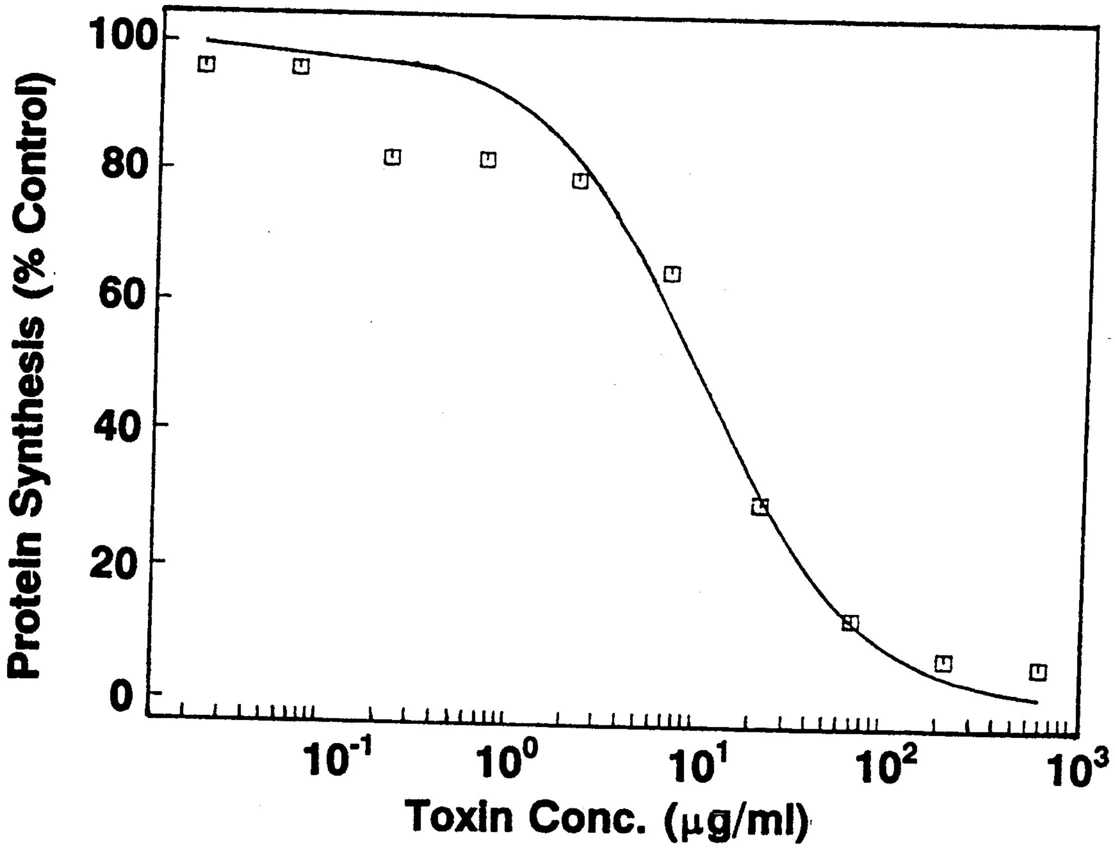
FIG. 6: Inhibition of protein synthesis in CF-1 cells by HD-73 toxin. Cells were incubated with the indicated concentrations of toxin for 20 minutes, then assayed for incorporation of $^{14}C$-leucine into protein as described in Materials and Methods. Results are expressed as a percentage of that obtained for CF-1 cells in the absence of toxin.

FIG. 6 demonstrates the inhibiting effect of HD-73 toxin on the incorporation of radiolabeled leucine into protein in CF-1 cells. Half-maximal inhibition was obtained at an HD-73 concentration of 40 μg/ml, in good agreement with the binding data presented above. Additional concurrence between HD-73 binding and inhibition of protein synthesis was established for the time-course and irreversibility of the inhibitory effect.

Figure 7:
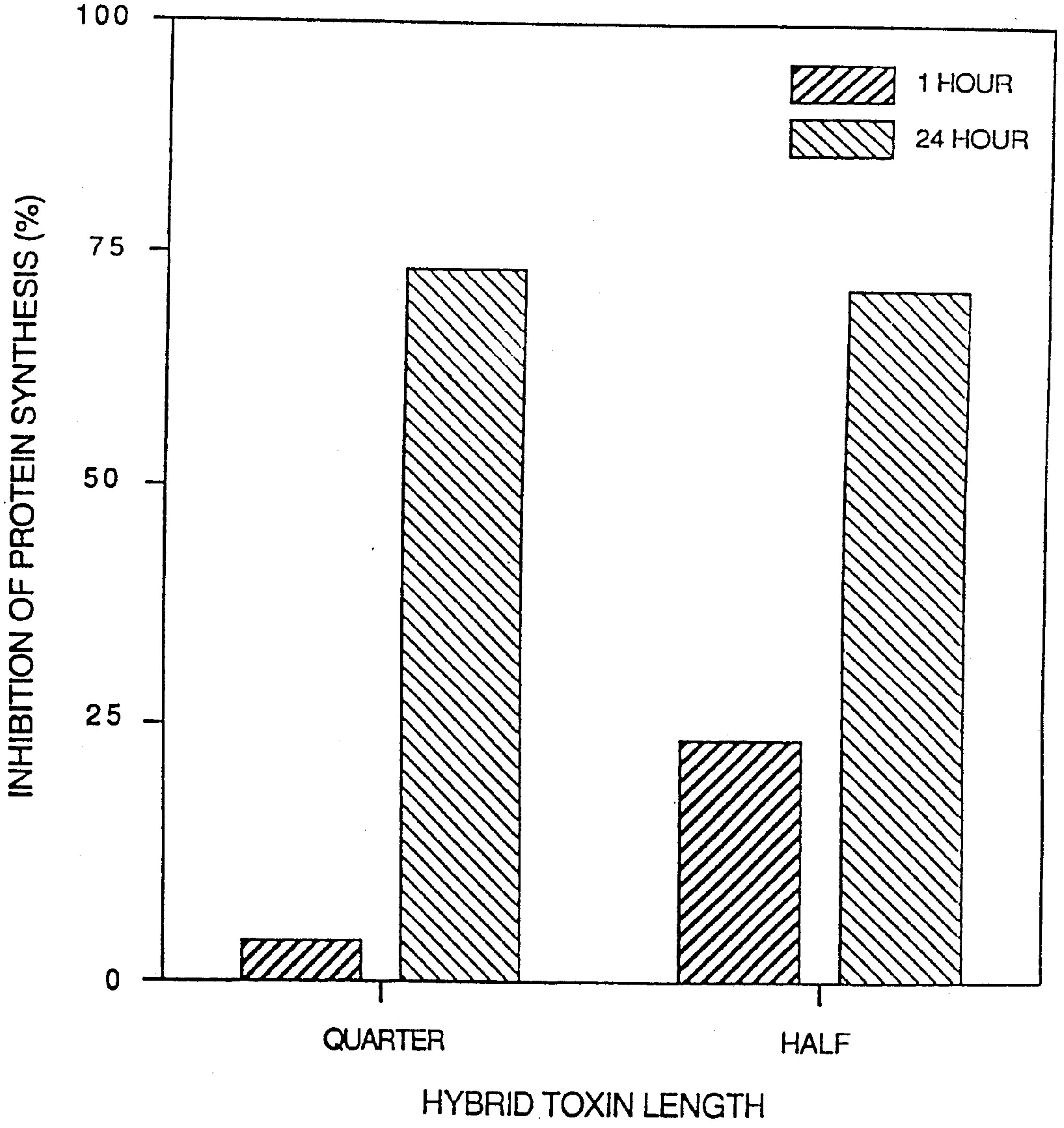
FIG. 7: Inhibition of protein synthesis in CF-1 cells by hybrid toxins. Cells were exposed to quarter or half length hybrid toxins for 1 or 24 hours, then assayed for $^{14}C$-leucine incorporation into protein as described in Materials and Methods. Percentage inhibition of protein synthesis was determined by comparison to control cells which were incubated for identical time intervals in the absence of hybrid toxins.

Incubation of CF-1 cells with quarter- and half-length hybrid toxins results in a slowly developing inhibition of protein synthesis (FIG. 7). From the 24-hour exposure data, we estimate a 50-fold increase in potency for the quarter-length and a 100-fold increase for the half-length hybrid toxin over that established for HD-73. The lengthened time-course and increased potency observed for the hybrid toxins indicate a mechanism of action distinct from that of HD-73. Furthermore, diphtheria toxin does not inhibit protein synthesis in CF-1 cells at concentrations up to 200 μg/ml. It is therefore unlikely that the inhibition produced by the hybrid toxin preparations is related to either the diphtheria or *B.t.* toxin domains by themselves, as might be the case if these two portions of the hybrid construct dissociated under experimental conditions. Rather, we conclude that these findings demonstrate an inhibitory mechanism unique to the intact hybrid toxins.

The various methods employed in the preparation of the plasmids and transformation of host organisms are well known in the art. These procedures are all described in Maniatis, T., Fritsch, E. F., and Sambrook, J. (1982) *Molecular Cloning: A Laboratory Manual,* Cold Spring Harbor Laboratory, New York. Thus, it is within the skill of those in the genetic engineering art to extract DNA from microbial cells, perform restriction enzyme digestions, electrophorese DNA fragments, tail and anneal plasmid and insert DNA, ligate DNA, transform cells, prepare plasmid DNA, electrophorese proteins, and sequence DNA.

The restriction enzymes disclosed herein can be purchased from Bethesda Research Laboratories, Gaithersburg, Md., or New England Biolabs, Beverly, Mass. The enzymes are used according to the instructions provided by the supplier.

A subculture of the host containing plasmid p26, also known as pMYC26, is presently on deposit in the Mycogen Corporation Culture Collection at San Diego, Calif. It was deposited on May 10, 1988 in the permanent collection of the Northern Research Laboratory, U.S. Department of Agriculture, Peoria, Ill., USA. It was assigned the deposit number NRRL B-18367. It was deposited in an *E. coli* host as *E. coli* HB101 (pMYC26). MR382 The plasmid can be obtained from the host by use of standard procedures, for example, using cleared lysate-isopycnic density gradient procedures, and the like.

The subject culture was deposited under conditions that assure that access to the culture will be available during the pendency of this patent application to one determined by the Commissioner of Patents and Trademarks to be entitled thereto under 37 CFR 1.14 and 35 USC 122. The deposit will be available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposit will be stored and made available to the public in accord with the provisions of the Budapest Treaty for the Deposit of Microorganisms, i.e., it will be stored with all the care necessary to keep it viable and uncontaminated for a period of at least five years after the most recent request for the furnishing of a sample of the deposit, and in any case, for a period of at least 30 (thirty) years after the date of deposit or for the enforceable life of any patent which may issue disclosing the culture. The depositor acknowledges the duty to replace the deposit should the depository be unable to furnish a sample when requested, due to the condition of the deposit. All restrictions on the availability to the public of the subject culture deposit will be irrevocably removed upon the granting of a patent disclosing it.

We claim:

1. Toxin active against lepidopteran insects having the amino acid sequence shown in FIG. 10 and mutations thereof in which the protein secondary structure is maintained.

2. Toxin active against lepidopteran insects having the amino acid sequence shown in FIG. 11 and mutations thereof in which the protein secondary structure is maintained.

* * * * *

UNITED STATES PATENT AND TRADEMARK OFFICE

CERTIFICATE OF CORRECTION

PATENT NO. : 5,290,914

DATED : March 1, 1994

INVENTOR(S) : Wilcox *et al.*

It is certified that error appears in the above-identified patent and that said Letters Patent is hereby corrected as shown below:

Column 2, line 18: After "B.t's" insert --which--.
Column 2, line 41: Delete "HD2" and insert --HD224--.
Column 15, line 16: After "Serratia" delete "." and insert --,--.
Column 16, lines 5-6: Delete "5′ to direction" and insert --5′ to 3′ direction--.
Column 17, line 53: Delete "Des ulfov ibrio," and insert --Desulfovibrio,--.
Column 19, line 56: Delete "amino-terminal terminal end" and insert --amino-terminal end--.
Column 27, line 26: After "Serine (Ser)" insert --QRS--
Column 28, lines 26-27: Delete "600 respectively" and insert --600 mCi/mmol, respectively."
Column 31, line 4: After "(pMYC26)" delete --.--.

Signed and Sealed this

Second Day of August, 1994

Attest:

BRUCE LEHMAN

*Attesting Officer* *Commissioner of Patents and Trademarks*